United States Patent
Padmanabhan et al.

(10) Patent No.: US 8,273,294 B2
(45) Date of Patent: Sep. 25, 2012

(54) MOLDED CARTRIDGE WITH 3-D HYDRODYNAMIC FOCUSING

(75) Inventors: Aravind Padmanabhan, Plymouth, MN (US); Ron L. Bardell, St. Louis Park, MN (US)

(73) Assignee: Honeywell International Inc., Morristown, NJ (US)

( * ) Notice: Subject to any disclaimer, the term of this patent is extended or adjusted under 35 U.S.C. 154(b) by 869 days.

(21) Appl. No.: 11/428,370

(22) Filed: Jun. 30, 2006

(65) Prior Publication Data

US 2007/0009386 A1    Jan. 11, 2007

Related U.S. Application Data

(60) Provisional application No. 60/696,162, filed on Jul. 1, 2005.

(51) Int. Cl.
*G01N 21/00* (2006.01)
*G01N 33/00* (2006.01)
*G01N 1/10* (2006.01)
*G01N 7/00* (2006.01)
*G01N 35/08* (2006.01)

(52) U.S. Cl. ............. 422/63; 422/50; 422/68.1; 422/73; 436/52; 436/148; 436/180

(58) Field of Classification Search .................. None
See application file for complete search history.

(56) References Cited

U.S. PATENT DOCUMENTS

| | | |
|---|---|---|
| 3,822,095 A | 7/1974 | Hirschfeld |
| 3,928,094 A | 12/1975 | Angell |
| 3,976,862 A | 8/1976 | Curbelo |
| 4,284,412 A | 8/1981 | Hansen et al. |
| 4,478,076 A | 10/1984 | Bohrer |
| 4,478,077 A | 10/1984 | Bohrer et al. |
| 4,501,144 A | 2/1985 | Higashi et al. |
| 4,599,000 A | 7/1986 | Yamada |
| 4,651,564 A | 3/1987 | Johnson et al. |
| 4,683,159 A | 7/1987 | Bohrer et al. |
| 4,695,034 A | 9/1987 | Shimizu et al. |
| 4,704,033 A | 11/1987 | Fay et al. |
| 4,745,279 A | 5/1988 | Karkar et al. |
| 4,818,263 A | 4/1989 | Mitch |

(Continued)

FOREIGN PATENT DOCUMENTS

DE    10122321    4/2002

(Continued)

OTHER PUBLICATIONS http://www.micronics.net/tsensor.htm, pp. 1-4, downloaded Jun. 14, 2000.

(Continued)

*Primary Examiner* — Neil N Turk
(74) *Attorney, Agent, or Firm* — Seager Tufte & Wickhem LLC.

(57) ABSTRACT

A microfluidic circuit cartridge having 3-D hydrodynamic focusing. The cartridge may be fabricated with injection-molded or other molded layers providing a 3-D structure. A flow channel on the card may have a sample core flowing in a fluid of a flow channel for analysis. The sample core may be adjustable in position within the channel with one or more jets or channels of fluid being injected into the flow channel. The jets may also adjust the size of the sample core. There may be a hemoglobin measurement mechanism or card with a cuvette.

11 Claims, 26 Drawing Sheets

U.S. PATENT DOCUMENTS

| | | | |
|---|---|---|---|
| 4,874,949 A | 10/1989 | Harris et al. | |
| 4,911,616 A | 3/1990 | Laumann, Jr. | |
| 4,932,989 A | 6/1990 | Presby | |
| 4,983,038 A * | 1/1991 | Ohki et al. | 356/246 |
| 5,017,497 A | 5/1991 | Gerard de Grooth et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,570,193 A | 10/1996 | Landa et al. | |
| 5,601,080 A | 2/1997 | Oppenheimer | |
| 5,616,501 A | 4/1997 | Rodriguez et al. | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,082,185 A | 7/2000 | Saaski | |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerle et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,382,228 B1 | 5/2002 | Cabuz et al. | |
| 6,506,609 B1 * | 1/2003 | Wada et al. | 436/148 |
| 6,537,501 B1 | 3/2003 | Holl et al. | |
| 6,549,275 B1 | 4/2003 | Cabuz et al. | |
| 6,576,194 B1 | 6/2003 | Holl et al. | |
| 6,597,438 B1 | 7/2003 | Cabuz et al. | |
| 6,729,856 B2 | 5/2004 | Cabuz et al. | |
| 6,767,190 B2 | 7/2004 | Cabuz et al. | |
| 6,970,245 B2 | 11/2005 | Fritz et al. | |
| 2003/0198523 A1 * | 10/2003 | Bohm et al. | 406/198 |
| 2004/0266022 A1 * | 12/2004 | Sundararajan et al. | 436/180 |
| 2005/0118723 A1 | 6/2005 | Padmanabhan et al. | |
| 2005/0243304 A1 | 11/2005 | Padmanabhan et al. | |

FOREIGN PATENT DOCUMENTS

| | | |
|---|---|---|
| EP | 0269076 | 6/1988 |
| EP | 1001326 | 5/2000 |
| EP | 1134548 | 9/2001 |
| JP | 61066947 | 4/1986 |
| JP | 10073528 | 3/1998 |
| JP | 2000056228 | 2/2000 |
| WO | 9527199 | 10/1995 |
| WO | 9843066 | 10/1998 |
| WO | 9960397 | 11/1999 |
| WO | 0109598 | 2/2001 |
| WO | 0210713 | 2/2002 |
| WO | 0210714 | 2/2002 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using a Prototype Microfluidics-Based Hematology Analyzer", SPIE Biomedical Optics 97, 1997.

Altendorf et al., "Differential Blood Cell Counts Obtained Using a Microchannel Based Flow Cytometer", Solid State Sensors & Actuators, vol. 1, 531, 1997.

Altendorf et al., "Implementation of Novel Optical Detection Methods for Clinically Important Blood Analytes Using Microfabricated Flow Structures (T-Sensors™)", MicroTAS 98, Banff, Canada, Apr. 1998.

Altendorf et al., "Microfabrication Technology for Research and Diagnostics, Silicon Microchannel Optical Flow Cytometry", SPIE Proceedings, Biomedical Optics 96, Jan. 1996.

Cabuz et al., "Mesoscopic Sampler Based on 3D Array of Electrostatically Activated Diaphragms", The 10th Int. Conf. On Solid-State Sensors and Actuators, Transducers'99, Sendai Japan, p. 1890-1, Jun. 7-12, 1999.

Darling et al., "Integration of Microelectrodes With Etched Microchannels for In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, pp. 13-18, Feb. 11-15, 1996.

Hatch et al., "Microfluidic Approaches to Immunoassays", SPIE conference on Micromachining and Microfabrication Symposium at Santa Clara, CA, 4 pages, Sep. 20-22, 1999.

Huang et al., "Development of a Flow Cytometry Based Miniature Chemical Fluid Analysis System Using Fluorescent Microbeads", SPIE Biomedical Optics, BIOS 97, conference proceedings, 8 pages, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, pp. 95-98, Feb. 11-14, 1990.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", Third Edition, p. 237, 1995.

Strzelecka et al., "Parallel Free-Space Optical Interconnect Based on Arrays of Vertical-Cavity Lasers and Detectors with Monolithic Microlenses", Applied Optics, v. 37(14), pp. 2811-2821, May 10, 1998.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3rd International Conference on Micro Opto Electro Mechanical Systems (MOEMS 99), Mainz, Germany, pp. 165-170, Aug. 30-Sep. 1, 1999.

Toshiyoshi et al., "Surface micromachined 2D Lens Scanner Array", Proc. IEEE?LEOS International Coference on Optical EMMS/ Sheraton Kauai Resort, Kauai, Hawaii, 3 pages, Aug. 21-24, 2000.

Tuantranont et al., "Flip Chip Integration of Lenslet Arrays on Segmented Deformable Micromirrors", Part of the Symposium on Design, Test and Microfabrication of MEMS and MOEMS, Paris, France, SPIE vol. 3680, 0277-786X/99 pp. 668-678, Mar.-Apr. 1999.

Tuantranont et al., "MEMS-Controllable Microlens Array for Beam Steering and Precision Alignment in Optical Interconnect Systems", Solid-State Sensor and Actuator Workshop, Hilton Head Island, South Carolina, Jun. 4-8, pp. 101-104, 2000.

Weigl et al, "Silicon-Microfabricated Diffusion-Based Optical Chemical Sensor", Reprint from "Sensors & Actuators" B 38-39, 452-457, 1997.

Weigl et al, "Microfluidic Diffusion-Based Separation and Detection", Science, vol. 283, pp. 346-347, Jan. 15, 1999.

Weigl et al, "Optical and Electrochemical Diffusion-Based Detection of Analytes in Complex Samples Using Microfabricated Flow Structures (T-SensorSTM)", Micro- and Nanofabricated Electro-Optical Mechanical Systems for Biomedical and Environmental Applications II—SPIE vol. 3606, Jan. 25-26, 1999.

Weigl et al, "Simultaneous Self-Referencing Analyte Determination in Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection in Silicon Flow Structures," Analytical Methods & Instrumentation, µTTAS 96 Special Edition, 21 pages, 1996.

Weigl et al., "Fluorescence and Absorbance Analyte Sensing in Whole Blood and Plasma Based on Diffusion Separation in Silicon-Microfabricated Flow Structures (T-Sensors™)," Biomedical Optics, vol. 6, No. 1, 11 pages, Jul. 1997.

Weigl et al., "Rapid Sequential Chemical Analysis Using Multiple Fluorescent Reporter Beads," µTTAS 96 Conference Proceedings, 1 page, 1996.

Weigl, "Microfluidic Diffusion Based Electrochemical Detection Using Microfabricated Flow Structures (T-Sensors™)," Analytical Chemistry, 18 pages, submitted 1999.

Weigl, "Whole Blood Assays Using Microfluidics-Based T-SensorSTm Technology", Medical Design Online, http://news.medicaldesignonline.com/featuresarticles/19990416-5922.html, 4 pages, Apr. 1999.

Yager et al., "Applying Microfluidic Chemical Analytical Systems to Imperfect Samples", Micro Total Analysis Systems 98, D. Harrison & A. van den Berg (ed.), Kluwer Academic Publishers, Dordrecht, pp. 207-212, 1998.

Yager et al., "Design of Microfluidic Sample Preconditioning Systems for Detection of Biological Agents in Environmental Samples", Yager, M. et al., SPIE Proceedings, vol. 3515, pp. 252-259, 1998.

* cited by examiner

| Channel | Volume {µl} | Height {mm} | Nominal Width {mm} | Channel Path |
|---|---|---|---|---|
| Whole Blood Sample | 12±2 | 0.100 (-0.015,+0.025) | 1.30 | Connects sample introduction port to Sample Injectors for both WBC and RBC Dilution channels. |
| WBC Dilution | 16±2 | 0.100 (-0.015,+0.025) | 1.32 | Connects Sample Injectors to Diluted Sample Injector. |
| RBC Dilution | 20±2 | 0.100 (-0.015,+0.025) | 1.32 | Connects Sample Injectors to Diluted Sample Injector. |
| Sheath | 2000±100 | 0.150±0.030 | 1.4 | Connects sheath fluid Storage Reservoir to Diluted Sample Injectors. |

FIGURE 6

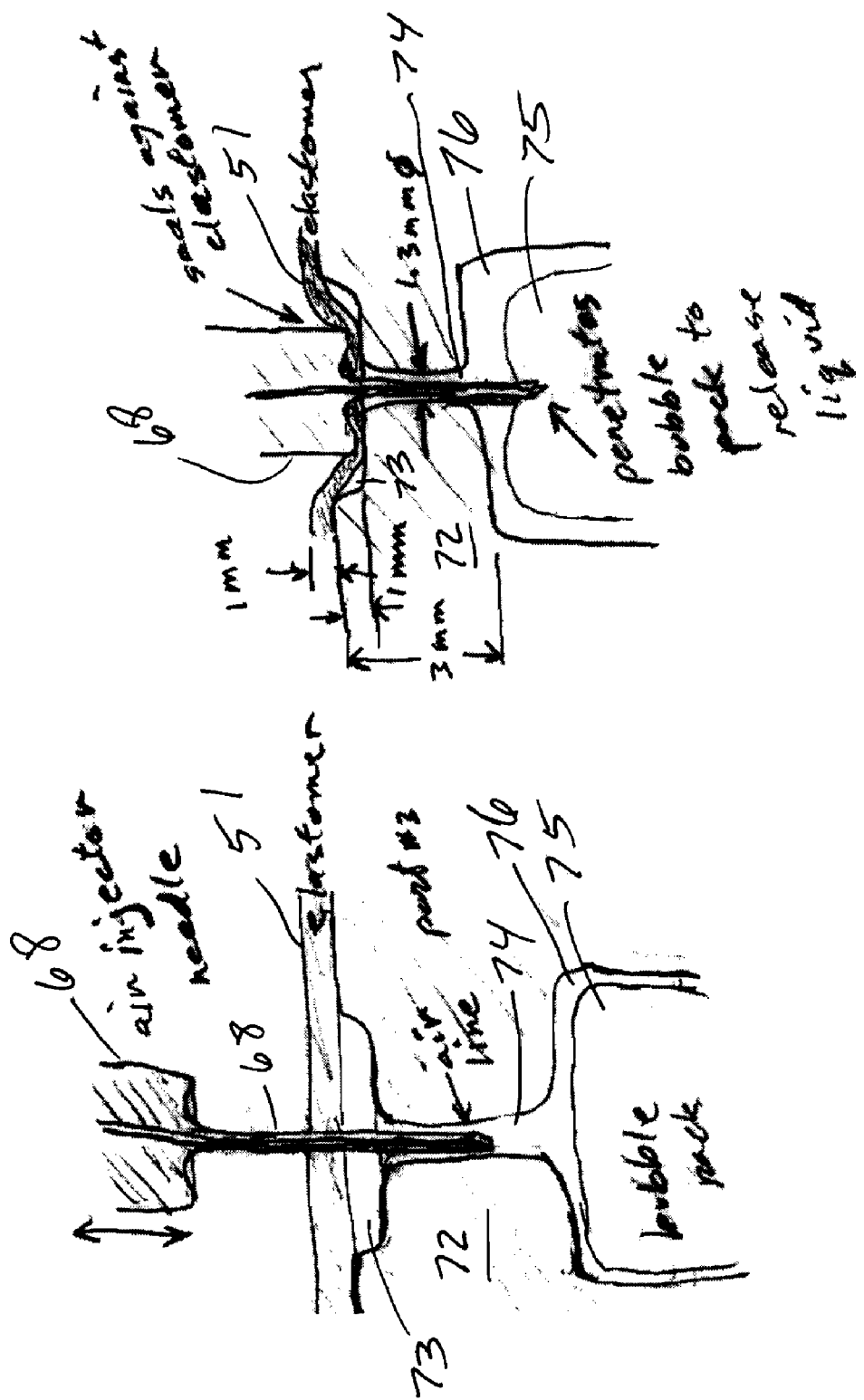

| Layer Number | Material | Nominal Thickness {mils} | Thickness range of material {mils} | Allowable Total Variation Between Cards Within 1 Lot {mils (mm)} |
|---|---|---|---|---|
| 121 | PMMA | 60 | 54 < t < 66 | 12 (0.300) |
| 122 | ACA | 6 | 5.4 < t < 6.6 | 1.2 (0.030) |
| 123 | PET | 2 | 1.98 < t < 2.02 | 0.4 (0.01) |
| 124 | ACA | 4 | 3.9 < t < 4.1 | 0.8 (0.02) |
| 125 | PMMA | 60 | 54 < t < 66 | 12 (0.300) |
| 126 | ACA | 6 | 5.4 < t < 6.6 | 1.2 (0.030) |
| 127 | PMMA | 60 | 54 < t < 66 | 12 (0.300) |

FIGURE 18

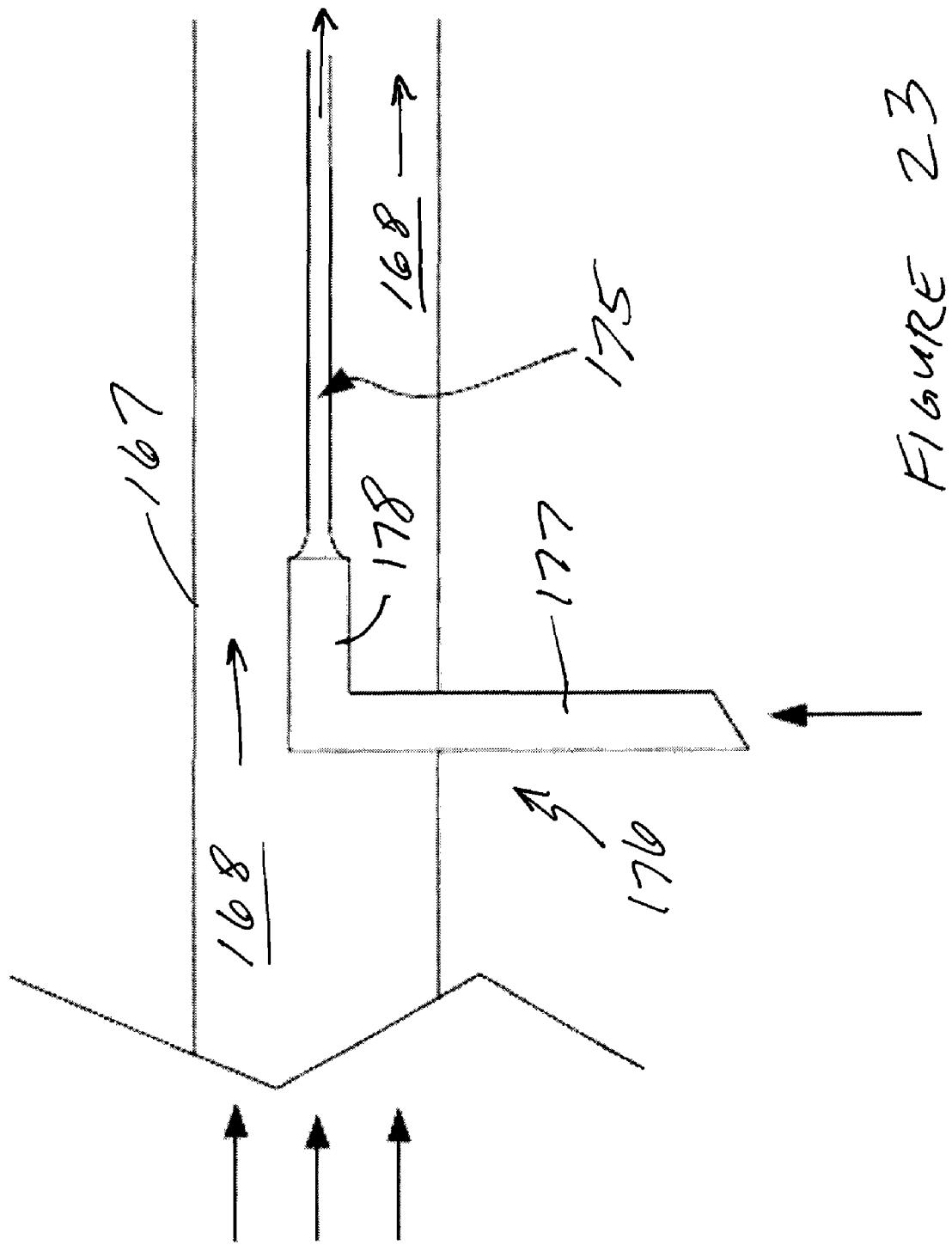

MOLDED CARTRIDGE WITH 3-D HYDRODYNAMIC FOCUSING

The present invention claims the benefit of U.S. Provisional Patent Application No. 60/696,162, filed Jul. 1, 2005. U.S. Provisional Patent Application No. 60/696,162, filed Jul. 1, 2005, is hereby incorporated by reference.

BACKGROUND

The present invention pertains to analyzers and particularly to hematology analyzers. More particularly, the invention pertains to cartridges of the analyzers.

Patents and applications related to the present invention may include: U.S. Pat. No. 6,382,228, issued May 7, 2002, and entitled "Fluid Driving System for Flow Cytometry"; U.S. Pat. No. 6,597,438, issued Jul. 22, 2003, and entitled "Portable Flow Cytometry"; U.S. Pat. No. 6,970,245, issued Nov. 29, 2005, and entitled "Optical Alignment Detection System; U.S. Pat. No. 6,549,275, issued Apr. 15, 2003, and entitled "Optical Detection System for Flow Cytometry"; U.S. Pat. No. 5,836,750, issued Nov. 17, 1998, and entitled "Electrostatically Actuated Mesopump Having a Plurality of Elementary Cells"; U.S. patent application Ser. No. 11/027,134, filed Dec. 30, 2004, and entitled "Optical Detection System with Polarizing Beamsplitter;

U.S. patent application Ser. No. 10/908,543, filed May 16, 2005, and entitled "Cytometer Analysis Cartridge Optical Configuration"; and U.S. patent application Ser. No. 10/908,014, filed Apr. 25, 2005, and entitled "A Flow Control System of a Cartridge"; all of which are hereby incorporated by reference.

SUMMARY

The present invention may relate to a microfluidic design of a molded disposable analysis cartridge. The cartridge may be injection molded and three-dimensional in structure. The cartridge may provide three-dimensional focusing.

BRIEF DESCRIPTION OF THE DRAWING

FIG. 6 is a table of parameters for a number of components of the microfluidic circuit;

FIGS. 7a and 7b show an interface between an injection needle and a reagent reservoir;

FIG. 8b is a diagram with a sample coming in to a main channel with a reagent at a junction and proceeding on with focusing with fluid jets;

FIG. 18 shows a table of a list of materials and dimensions for the layers of the hemoglobin parameter measurement card; and FIGS. 19-23 show various configurations of sample core dimension and position adjustment control in a flow channel of an analyzer.

DESCRIPTION

Figure 1:
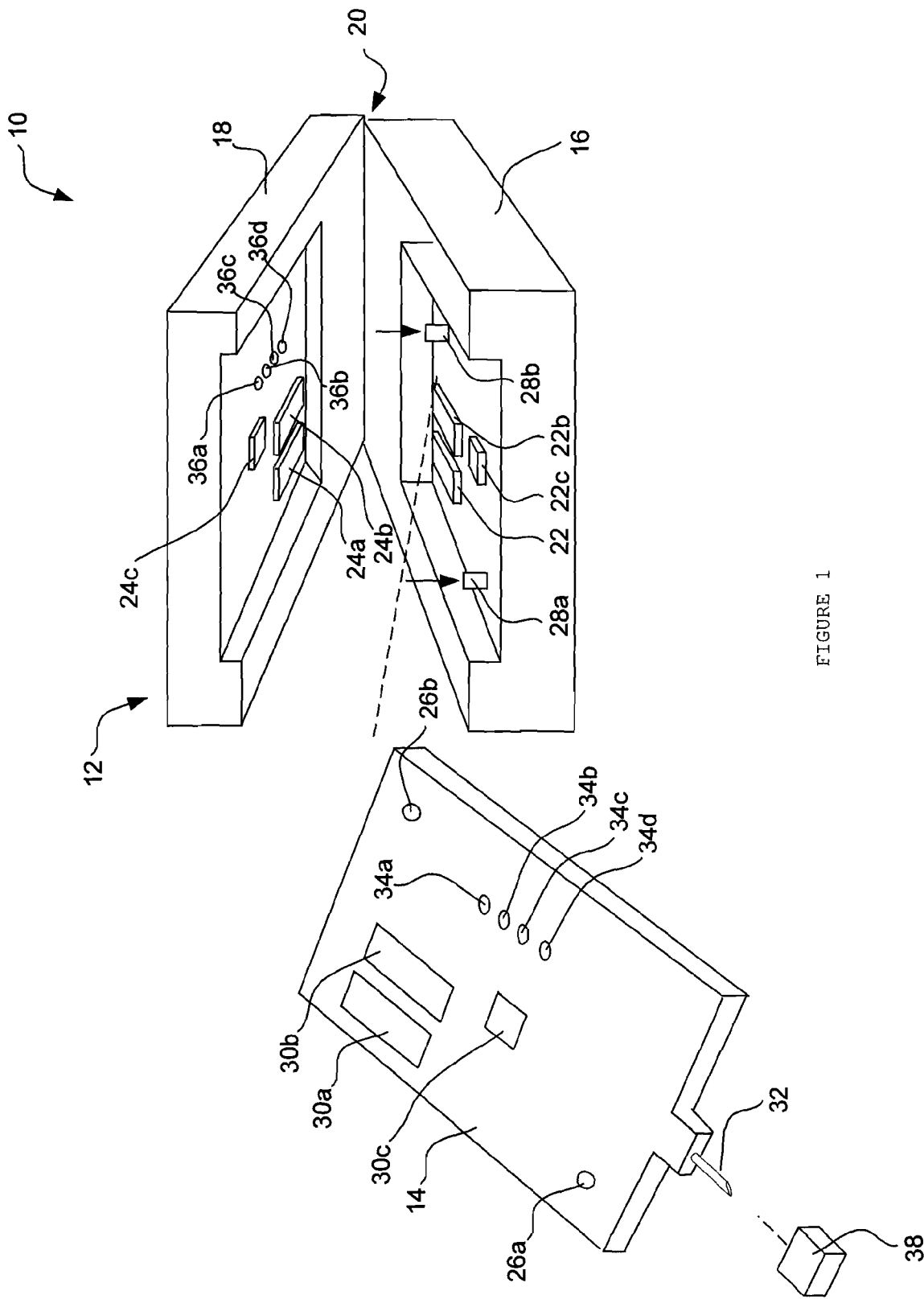
FIG. 1 is a block diagram of a particle counting and size measurement system.

The present invention generally relates to sample analyzers, and more particular, to sample analyzers with removable and/or disposable cartridges for use at the point of care of a patient such as in a doctor's office, in the home, or elsewhere in the field. By providing a removable and/or disposable cartridge with all of the needed reagents and/or fluids, the sample analyzer can be reliably used outside of the laboratory environment, with little or no specialized training. This may, for example, help streamline the sample analysis process, reduce the cost and burden on medical or other personnel, and increase the convenience of sample analysis for many patients, including those that require relatively frequent blood monitoring/analysis.

An approach which allows rapid and efficient particle discrimination in a particle-suspension sample is flow cytometry. In this approach, a suspension of particles, typically cells in a blood sample, is transported through a flow channel where the individual particles in the sample are illuminated with one or more focused light beams. The interaction of the light beam(s) with the individual particles flowing through the flow channel is detected by one or more light detectors. Commonly, the detectors are designed to measure light absorption or fluorescence emission, at specific beam or emission wavelengths, and/or light scattering at specific scattering angles. Thus, each particle that passes through the flow channel can be characterized as to one or more features related to its absorption, fluorescence, light scattering or other optical or electrical properties. The properties that are measured by the detectors may allow each particle to be mapped into a feature space whose axes are the light intensities or other properties which are measured by the detectors. In the ideal, the different particles in the sample map into distinct and non-overlapping regions of the feature space, allowing each particle to be analyzed based on its mapping in the feature space. Such analysis may include counting, identifying, quantifying (as to one or more physical characteristics) and/or sorting of the particles.

In one illustrative example may be a sample analyzer which is provided that has a removable cartridge that receives a collected sample, such as a collected whole blood sample, and once the removable cartridge is installed and the analyzer is activated, the analyzer and cartridge automatically process the sample and the analyzer provides sufficient information for the user to make a clinical decision. In some examples, the analyzer displays or prints out quantitative results (e.g., inside and/or outside of a predefined range), such that no further calculations or interpretation is required by the user.

The sample analyzer may be used to, for example, determine the number and/or types of white blood cells in a blood sample. In one illustrative example, the analyzer includes a housing and a removable fluidic cartridge, wherein the housing is adapted to receive the removable fluidic cartridge. In some cases, the removable fluidic cartridge is a disposable cartridge. In one illustrative example, the removable fluidic cartridge may include one or more reagents (e.g., sphering agents, lysing reagents, stain, and/or diluents), one or more analysis channels, one or more flow sensors, one or more valves, and/or a fluidic circuit that is adapted to process (e.g., sphere, lyse, stain, or other) a sample and deliver processed sample(s) to the appropriate analysis channel on the cartridge. To support the card, the housing may include, for example, a pressure source, one or more light sources, one or more light detectors, a processor and a power source. The pressure source may provide appropriate pressure(s) to the removable fluidic cartridge ports to drive the fluids as required through the fluidic circuit. The one or more light sources of the analyzer may be used to interrogate the prepared sample in at least selected analysis channels of the removable cartridge, and the one or more light detectors of the analyzer may detect the light that passes through, is absorbed by and/or is scattered by the sample. The processor may be coupled to at least some of the light sources and detectors, and may determine one or more parameters of the sample. In some examples, the one or more analysis channels on the removable fluidic cartridge may include one or more flow cytometry channels. In some illustrative examples, a whole blood sample may be provided to the removable fluidic cartridge, and the removable cartridge may be adapted to perform a rather complete blood analysis.

FIG. 1 is a perspective view of an illustrative sample analyzer and cartridge. The illustrative sample analyzer is generally shown at 10, and includes a housing 12 and a removable or disposable cartridge 14. The illustrative housing 12 includes a base 16, a cover 18, and a hinge 20 that attaches the base 16 to the cover 18, but this is not required. In the illustrative example, the base 16 includes a first light source 22a, a second light source 22b, and a third light source 22c, along with associated optics and the necessary electronics for operation of the sample analyzer. Each of the light sources may be a single light source or multiple light sources, depending on the application. In some cases, the overall dimensions of the housing may be less than 1 cubic foot, less than one-half cubic foot, less than one-quarter cubic foot, or smaller, as desired. Likewise, the overall weight of the housing may be less than 10 pounds, less than 5 pounds, less than one pound, or less, as desired.

The illustrative cover 12 includes a pressure source (e.g. pressure-chambers with control microvalves), a first light detector 24a, a second light detector 22b, and a third light detector 22c, each with associated optics and electronics. Each of the light detectors may also be a single light detector or multiple light detectors, depending on the application. Polarizers and/or filters may also be provided, if desired, depending on the application.

The illustrative removable cartridge 14 is adapted to receive a sample fluid via a sample collector port, which in the illustrative example, includes a lancet 32. The lancet 32 may be retractable and/or spring loaded, in some examples. A cap 38 may be used to protect the sample collector port and/or lancet 32 when the removable cartridge 14 is not in use.

In the illustrative example, the removable cartridge 14 performs a blood analysis on a whole blood sample. The lancet 32 may be used to prick the finger of the user to produce a sample of blood, which through capillary action, may be drawn into an anti-coagulant coated capillary in the removable cartridge 14. The removable cartridge 14 may be constructed with the fluidic circuits, some of which are fabricated using a structure with etched, machined or molded channels. However, it is contemplated that the removable cartridge 14 may be constructed in any suitable manner including by injection molding or any other suitable manufacturing process or approach, as desired.

During use, and after a blood sample has been drawn into the removable cartridge 14, the removable cartridge 14 may be inserted into the housing when the cover 18 is in the open position. In some cases, the removable cartridge 14 may include holes 26a and 26b for receiving registration pins 28a and 28b in the base 16, which may help provide alignment and coupling between the different parts of the instrument. The removable cartridge 14 may also include a first transparent flow stream window 30a, a second transparent flow stream window 30b and a third transparent window 30c, which are in alignment with the first, second and third light sources 22a, 22b and 22c, and the first, second and third light detectors 24a, 24b and 24c, respectively.

When the cover is moved to the closed position, and the system is pressurized, the cover 18 may provide controlled pressures via pressure providing ports 36a, 36b, 36c, and 36d to pressure receiving ports 34a, 34b, 34c and 34d, respectively, in the illustrative removable cartridge 14. It is contemplated that more or less pressure providing and pressure receiving ports may be used, depending on the application. Alternatively, or in addition, it is contemplated that one or more micro-pumps, such as electrostatically actuated meso pumps, may be provided on or in the removable cartridge 14 to provide the necessary pressures to operate the fluidic circuit on the removable cartridge 14. Some illustrative electrostatically actuated meso pumps are described in, for example, U.S. Pat. Nos. 5,836,750, 6,106,245, 6179,586, 6,729,856, and 6,767,190, all of which are hereby incorporated by reference. Once pressurized, the illustrative instrument may perform a blood analysis on the collected blood sample.

Figure 2:
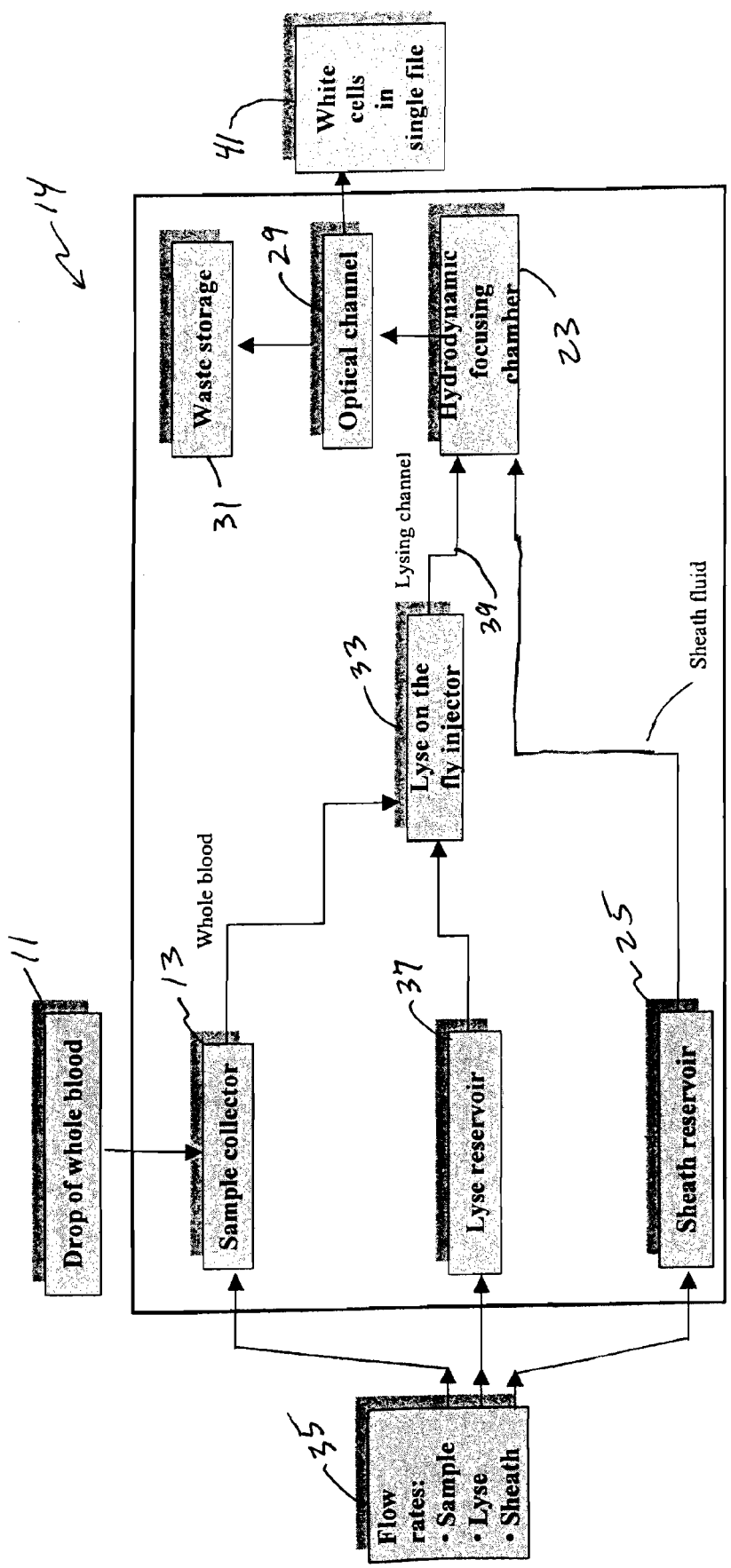
FIG. 2 shows a portion of an illustrative blood analysis cartridge for white blood cells.

FIG. 2 is a diagram showing some aspects of an illustrative example of a WBC portion of cartridge or card 14. One may start with a sample of whole blood 11 to a sample collator 13. The blood may be pushed on to a lyse on the fly injector 33. The flow rates for pushing the sample, and also the lysing and sheath fluids may be provided by a pump mechanism or flow rate control box 35. Lysing fluid for the lyse on the fly injector may come from a lyse reservoir 37. The lyse fluid and blood may proceed through a lysing channel 39 to a hydrodynamic focusing chamber 23. A sheathing fluid may go from a sheath reservoir 25 to the hydrodynamic focusing chamber 23 to aid in aligning white cells in a single file 41 through an optical channel 29 for detection and analysis. After the cells have proceeded to optical channel 29, the cells and fluid may move to a waste storage 31.

Figure 3:
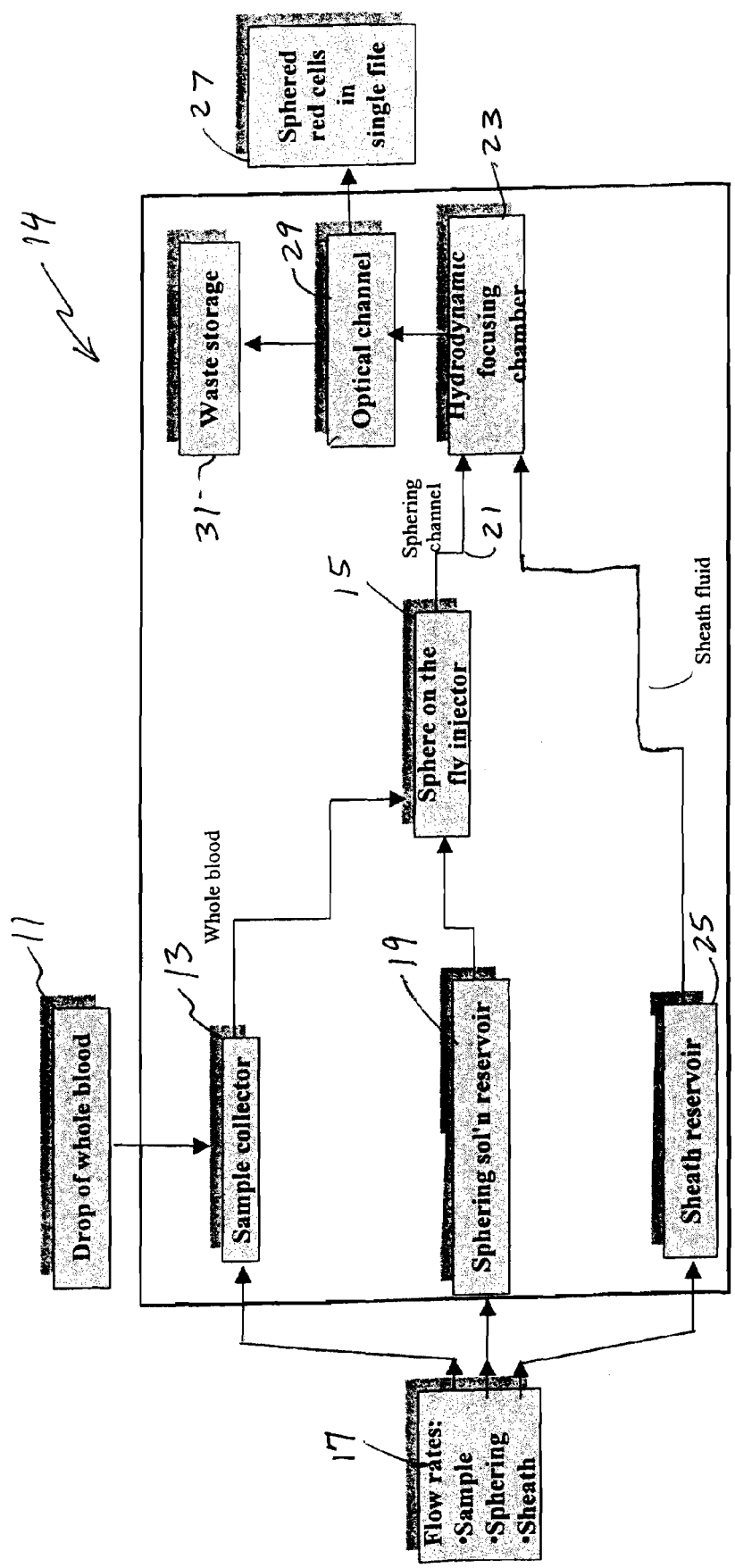
FIG. 3 shows a portion of the an illustrative blood analysis cartridge for red blood cells.

FIG. 3 is a diagram showing some of the aspects of an illustrative example of an RBC portion of cartridge or card 14. This card 14 may be similar to the WBC card 14 except that it may be designed for RBC analysis. Similarly, instrument 10 may be designed for RBCs. One may start with a sample of whole blood 11 going to a sample collator 13. The blood may be pushed to a sphere on the fly injector 15. The flow rates for pushing the sample, and also for the sphering and sheath fluids, may be provided by a pump mechanism or flow rate control box 17. Sphering fluid for the sphere on the fly injector 15 may come from a sphering solution reservoir 19. The solution and blood may proceed through a sphering channel 21 to a hydrodynamic focusing chamber 23. A sheathing fluid may go from a sheath reservoir 25 the hydrodynamic focusing chamber 23 to aid in aligning the sphered red cells in single file 27 through an optical channel 29 for detection and analysis. After the cells have proceeded through optical channel 29, the cells and fluid may move on to a waste storage 31.

Figure 4:
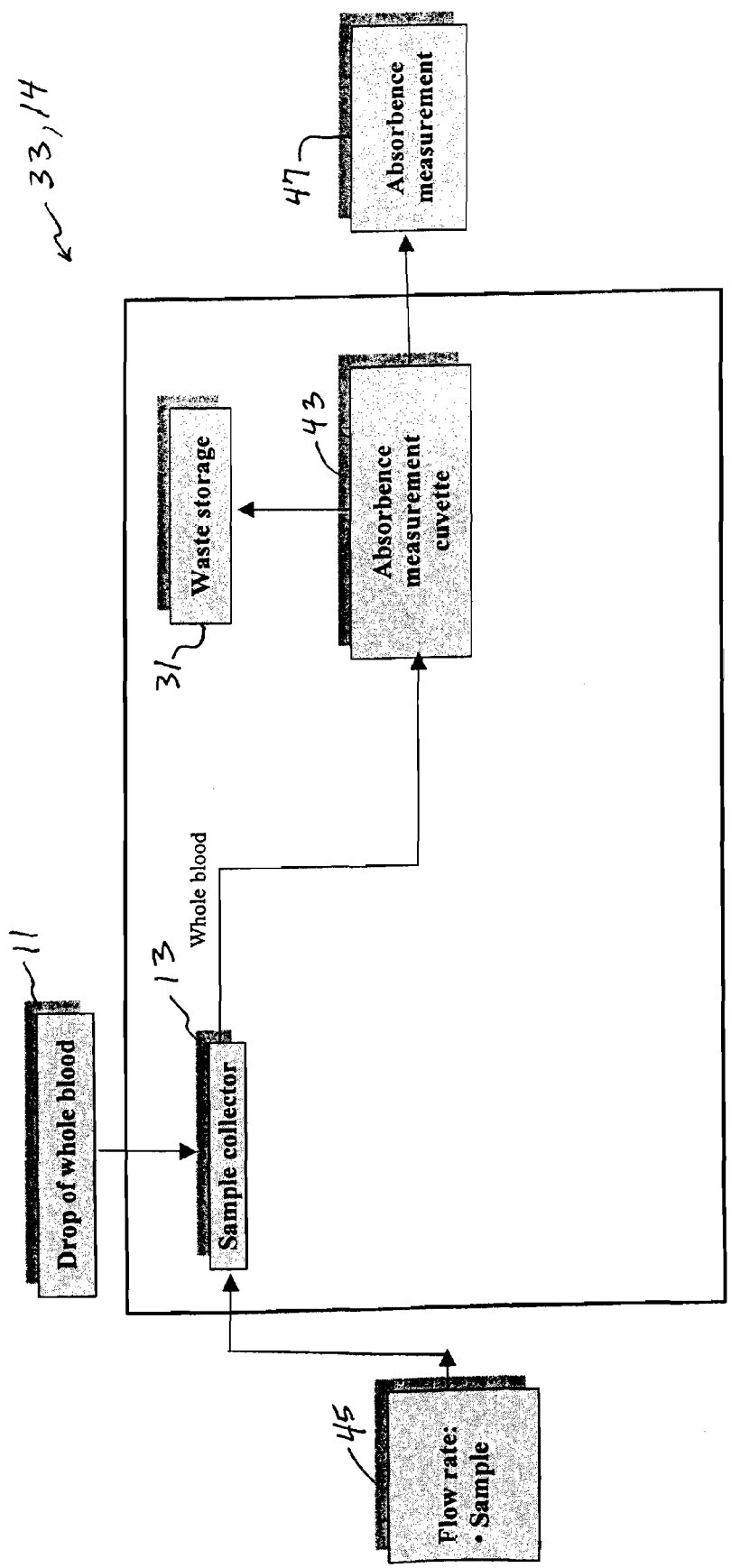
FIG. 4 shows a portion of the illustrative blood analysis cartridge for hemoglobin.

FIG. 4 is a diagram showing some aspects of an illustrative example of a hemoglobin (HGB) card 33 or HGB portion of cartridge or card 14. This card may be a substitute for, or combined with the WBC card 14, as is designed for HGB analysis. Similarly, instrument 10 may be designed for HGB measurement. One may start with a sample of whole blood 11 to a sample collector 13. The blood may be pushed on to an absorbence measurement cuvette 43. The flow rate for pushing the sample may be provided by a pump mechanism or flow rate control box 45. The blood may proceed through the absorbence measurement cuvette 43, which may provide an absorbence measurement 47. After the measurement, the blood may proceed on to a waste storage 31.

The present system may be a microfluidic design of a molded (as contrasted with a laminated) (i.e., the invention may include the molded version) disposable analysis cartridge. The cartridge may be injection molded and three-dimensional in structure. It may have fluidic features to perform various functions like sample dilution, sample lysing, sample sphering, hemoglobin measurements and analyses, hydrodynamic focusing, and so forth.

The present system may provide a complete blood count (CBC) card based on a micro-scale flow cytometer or hematology analyzer for obtaining one or more of the following items including red blood cell (RBC) counts, sphering RBCs, platelet counts, lysis of RBCs, multi-part differential counts of white blood cells (WBCs), hemoglobin absorbence-based measurements, various additional indices of RBCs, platelets, WBCs, hemoglobin, and so forth, plus hydrodynamic focusing to create single-file streams of cells, and a pneumatic fluid driver system. Additional items may be provided by and/or be a part of the present system.

Figure 5:
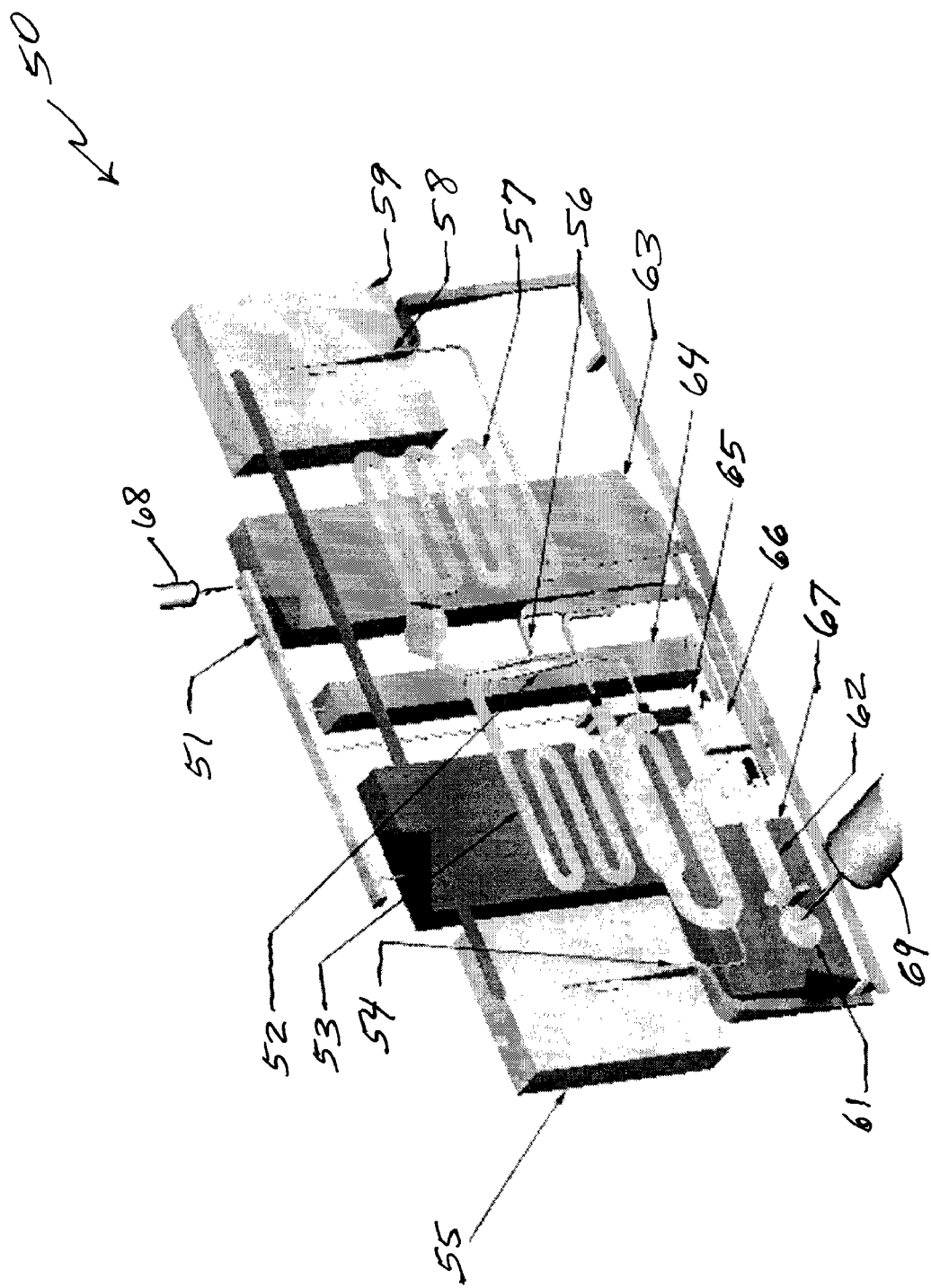
FIG. 5 shows a pipe network of a complete blood count card.

Several CBC card configurations are noted. One may be a dry interface card with onboard reagents storage and flow sensors, and with fluids driven by pneumatic pressure sources. Another configuration may be a wet interface card with fluids supplied by volumetric-based delivery from off-card reagent storage and flow sensors. FIG. 5 shows a dry interface card 50. The wet interface card may differ with an omission of the stored reagents, flow sensors, and two out of four needle inserts.

FIG. 5 shows a pipe network of the CBC card 50. Card or cartridge 50 may have various components that may be arranged and connected in a similar manner as those on cartridge 14 and analyzer 10 described herein (FIGS. 1-4). FIG. 5 shows an elastomer 51 for air injection, an RBC sample injector 52, an RBC dilution channel 53, an RBC focusing chamber 54 and an RBC optics cutout 55. Towards the other end of card 50, FIG. 5 shows a WBC sample injector 56, a WBC dilution channel 57, a WBC focusing chamber 58 and a WBC optics cutout 59. Also shown on card 50 are an elastomer 61 for blood injection, a blood sample channel 62, a sheath fluid tank 63, a lyse fluid tank 64, a pusher fluid tank 65, flow sensors 66 and a waste fluid tank 67. There may be other components as needed on card 50. Provisions and components may be included on card 50 for hemoglobin measurements and analyses. Tanks and channels may be voids formed by molded pieces put together to make up card 50. Bubble packs may be included for the tanks. Also shown are needle injectors 68 and 69 for air and blood injection, respectively.

Measurement channels on card 50 may be narrow channels at about the center of the optics cutouts in which the optical detectors may be located. The pipe network may be realized by voids in several injection-molded plastic parts. Air may be injected into the tanks to drive the fluids through the network and to the waste tank 67.

Microfluidic circuits of card 50 may have tolerances. Many of the components of the microfluidic circuit are long and narrow channels with volumes and cross-sections (width and height) as specified in the table of FIG. 6. The noted channel path locations may be in reference to FIG. 5. The height dimensions are the smallest and have the tightest tolerances since they most affect pressure loss, sedimentation rate, and diffusion speed in the channels. The channel widths and lengths may be nominal, but the volumes generally need tolerances.

FIGS. 7a and 7b show an interface between a pusher fluid (i.e., air) and a liquid reagent stored on card 50 in a blister or bubble pack 75. A septum or elastomer 51 may be pierced by a hollow injection needle 68 on a wider base 73 and through an air line 74 of card material 72 may provide a low-compliance and leak-free interface between a pusher fluid (e.g., air) and a liquid reagent stored on-card in the blister pack 75. The septum 51 may also function as a gasket that mates with the wide base of the needle 68 as shown in FIG. 7b.

Figure 8A:
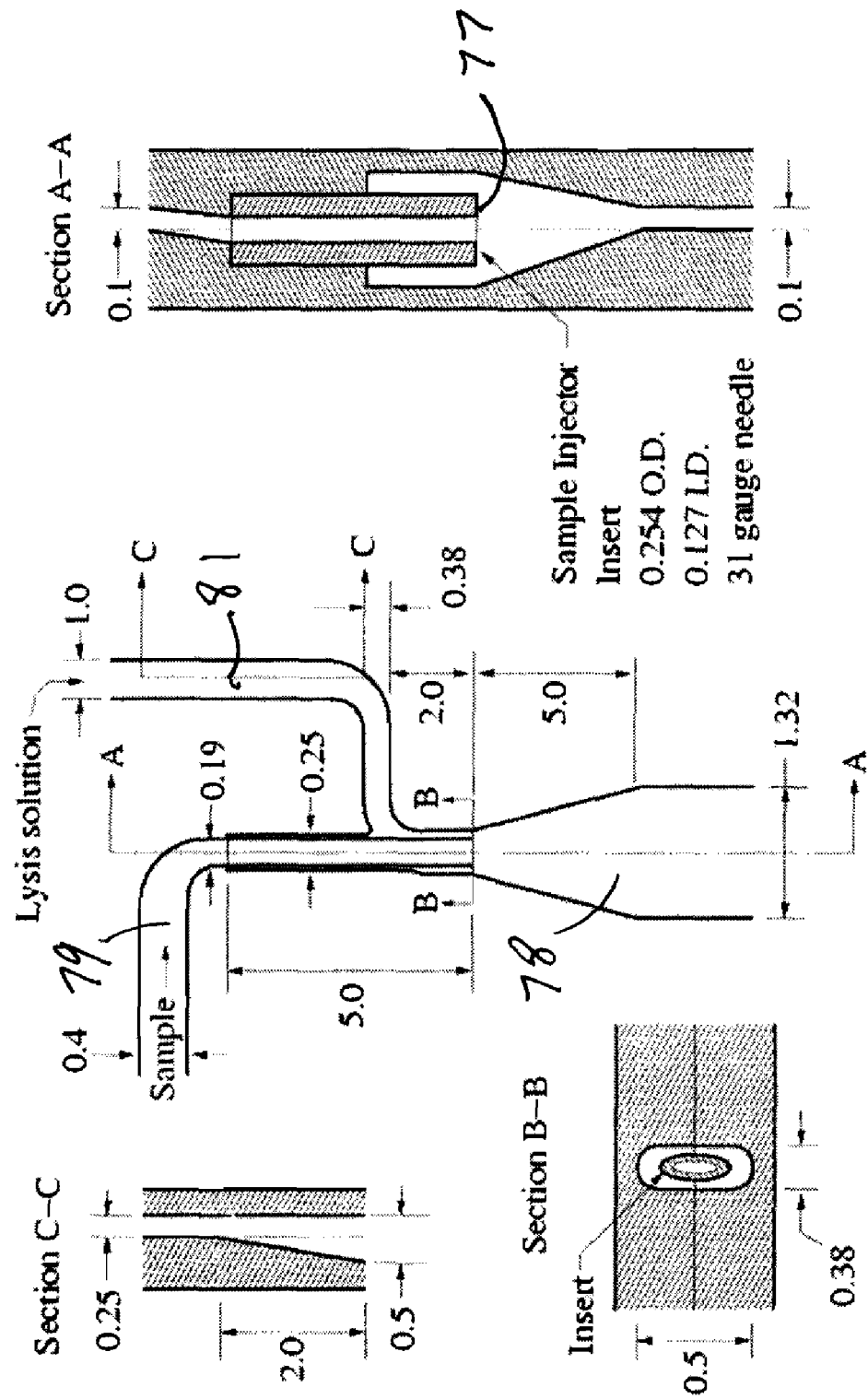
FIG. 8a shows an injector for providing a sample into a stream of a fluid.
Figure 86:
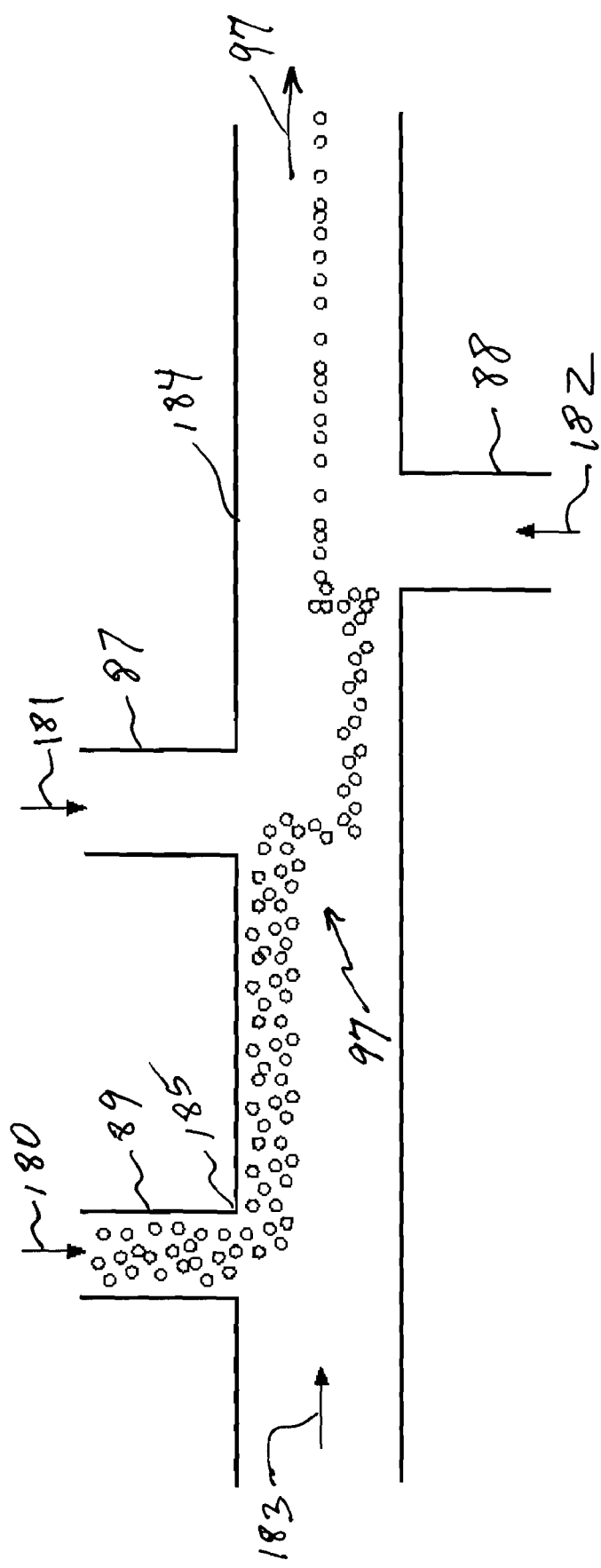

FIG. 8a shows a drawing having dimensions in millimeters with section views of an injection-molded assembly having a sample injector 77 (with #31 gauge needle insert). The thickness dimension is magnified about 5 times in Sections A-A and B-B for clarity. The channels are not necessarily round in cross-section, but may be rectangular, with small filets, or molded or machined corners. A tolerance of +/−15 percent appears sufficient on all dimensions, except where the needle is inserted, straddling the parting line. An interference fit may be suggested there to prevent leakage around the needle. A sample stream 79 may be injected into the center of a solution stream 81, which then could proceed to the channel 78. The tightest tolerances in this component may be the interference fit with the needle insert and the heights of the upstream and downstream channels in Section A-A that may be specified in the table of FIG. 6.

A molded device may permit a presence of smooth surfaces within various channels and chambers of the fluidic circuits. Such an approach may reduce or eliminate air bubbles and other anomalies that could occur with other fabrication approaches. For an illustrative example, a channel 186 may be rectangular or round in shape. A core stream with a reagent as a sheath around it may be circular in cross-section, both of which could increase or decrease proportionately, depending on the kind of channel or chamber is present to them during a flowing action. Three-D focusing may be effected here. A rectangular shaped channel 186 may have smooth corners due to molded components. It may be noted that an injected sample core into the channel may have a reagent around it, which can permit 3-D focusing of the sample core. The molded components may also be machined for achieving a particular shape in a channel or chamber. Other components such as injectors, jets, tanks, reservoirs, loops, and so forth, of a fluidic circuit may be molded components, or results or products of molded items, such as layers.

There may be several approaches to achieve hydrodynamic focusing of the sample stream into a narrow sample core stream, in which cells proceed in single file. A first approach may be a stream-wise variation of the cross-section of a focusing chamber. A second approach may be a stream-wise variation in the volume flow rate of the fluid in the channel by means of fluid jets emanating from side channels. Focusing of the sample stream into a single-file stream of cells may be accomplished by either approaches or a combination of the approaches.

In the first approach, the cross-section may be varied between the plane of injection (Section B-B in FIG. 8a) and the exit plane at the transition from focusing chamber to downstream channel. The change in position and size of the cell stream between the first and second planes may be directly proportional to the change in cross-section of the focusing chamber between these two planes.

The first approach may be implemented in a card fabricated in plastic laminates. However the shape of the focusing chamber may be implemented by a cutouts in the stack of plastic layers, thus the hydrodynamic focusing achieved in each layer is two-dimensional focusing. A drawback to this fabrication approach may be that the step changes in chamber cross-section as the cutouts shapes change from layer-to-layer provide sites that trap air bubbles, which alter the effective shape of the focusing chamber and may degrade its focusing performance.

The first approach may be implemented by rendering the shape of the focusing chamber in plastic injection-molded parts. These molds may be machined with compound curves that provide smoothly varying changes in the focusing chamber cross-section, minimizing the trapped air bubble problem.

The second approach may be implemented by series of fluid jets emanating a sheath fluid 181 and 182, and/or other reagent, from side channels or jets 87 and 88, respectively, as shown in FIG. 8b. This Figure shows a sample 180 coming into a main channel 184 via a channel or injector 89 and combining with a reagent 183 at a T-junction 185 and proceeding on with focusing from the side fluid jets 87 and 88. The T-junction 185 or a similar structure may reduce or eliminate clumping for some samples. This approach may focus the cell stream 97 in channel 184 without any change in channel cross-section by utilizing the laminar nature of fluid flow that is characteristic of liquids in microchannels. The fluid emanating from the side jets 87 and 88 may take up space in the channel, which could narrow and accelerate the fluid stream that is already in the channel. There may be more or less jets.

Figure 9A:
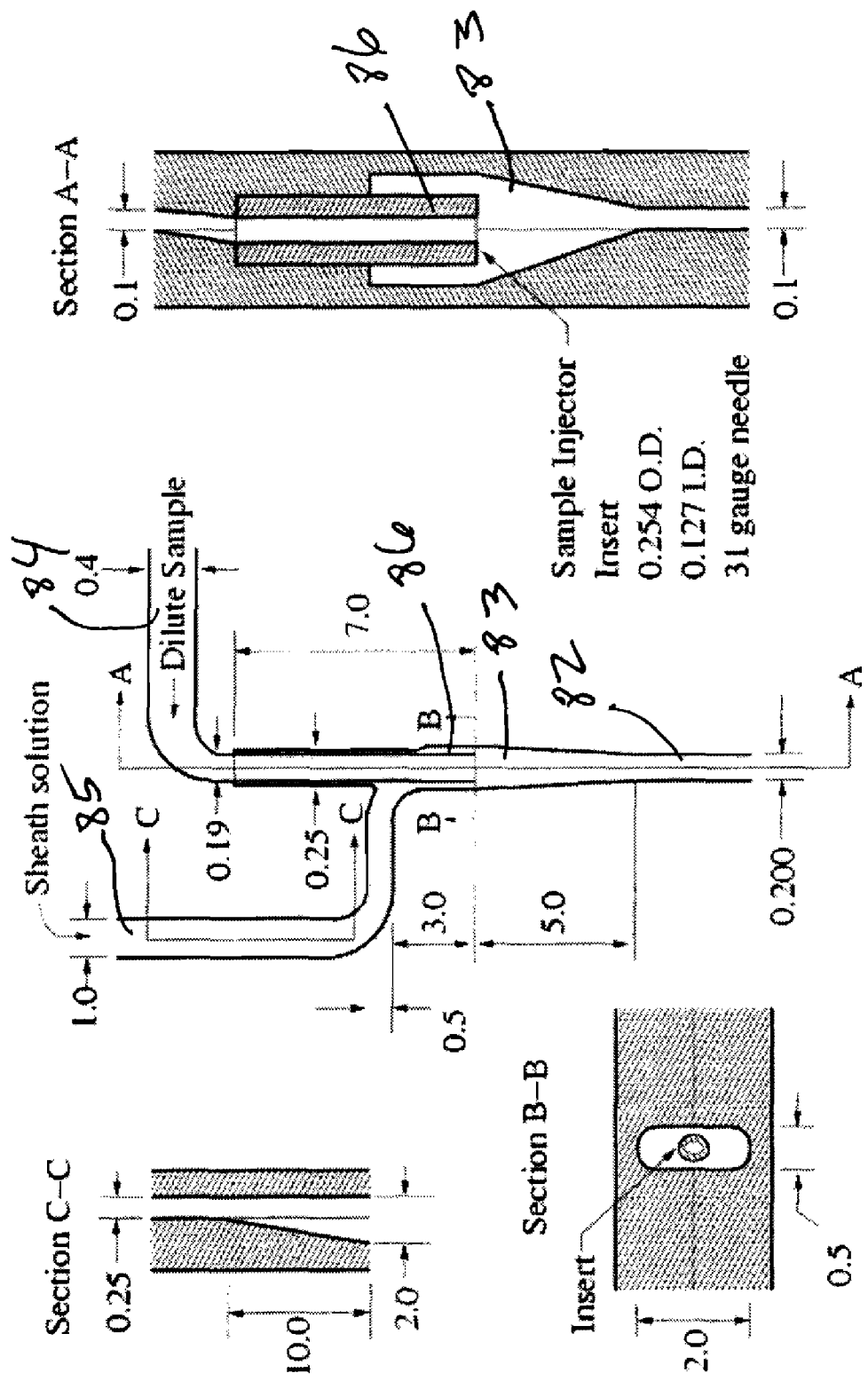
FIGS. 9a and 9b show another version of an injector for providing a sample into a stream of a fluid.

FIG. 9a shows a focusing chamber 83 and the beginning of a measurement channel 82. Components of FIG. 9a may be molded in the same or another manner as those in FIG. 8a. A diluted sample stream 84 may be injected into the center of the sheath fluid stream 85 and the streams may flow into the focusing chamber and measurement channel. As in the sample injector, the tightest tolerances in this component may be the interference fit with the needle insert and the heights of the upstream and downstream channels in Section A-A that are as specified in the table of FIG. 6.

Figure 9B:
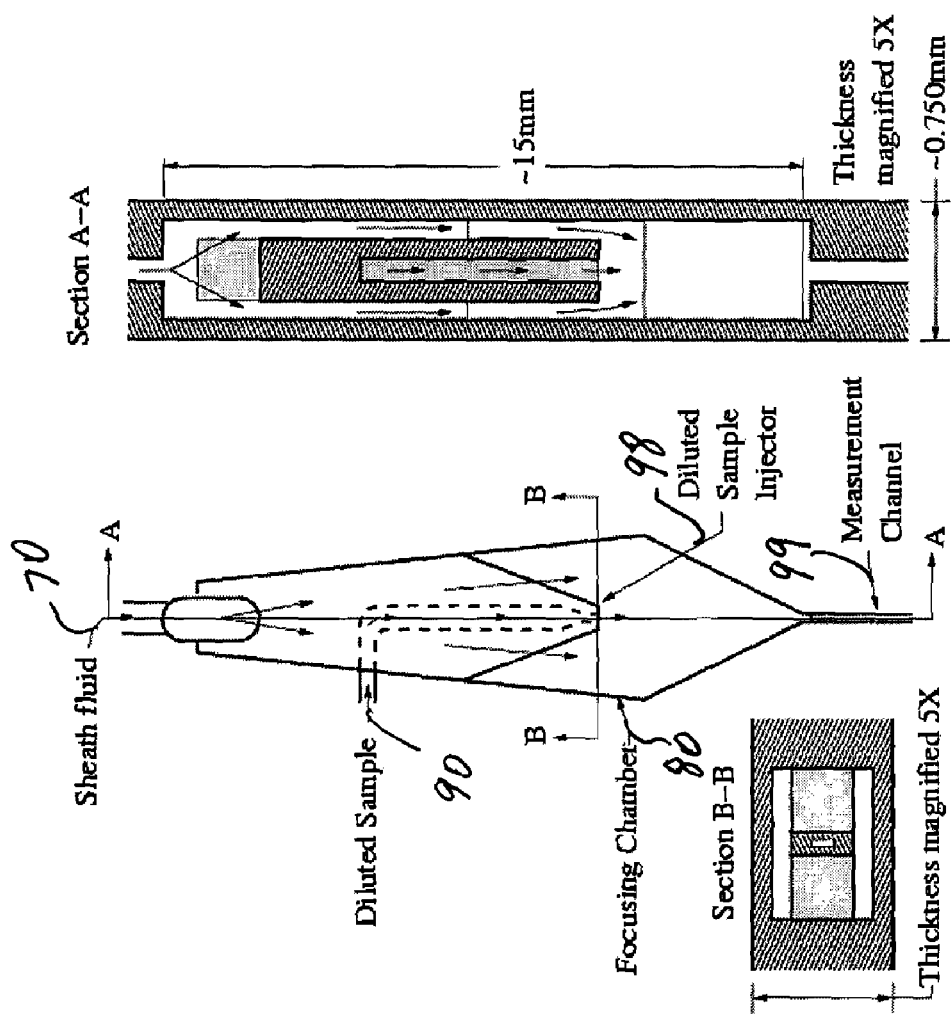

FIG. 9a shows dimensions in millimeters of a device which could be an injection-molded focusing chamber 83 and entry to the measurement channel 82 downstream. The thickness dimension has been magnified about 5 times in Section A-A for clarity. The channels are not necessarily round in cross-section, but rectangular, but possibly could have small filets placed in the corners or be machined or molded for smooth corners. A tolerance of +/−15 percent may be sufficient on all dimensions, except where the needle is inserted, straddling the parting line. An interference fit may be suggested there to prevent leakage around the needle. FIG. 9b shows an entry of a sheath fluid 70 towards a focusing chamber 80. A diluted sample 90 may be provided to the focusing chamber 80 by a diluted sample injector 98. The resultant flow may go to a measurement channel 99. Smoothly curved walls may eliminate bubble entrapment the various setups described herein.

Figure 10:
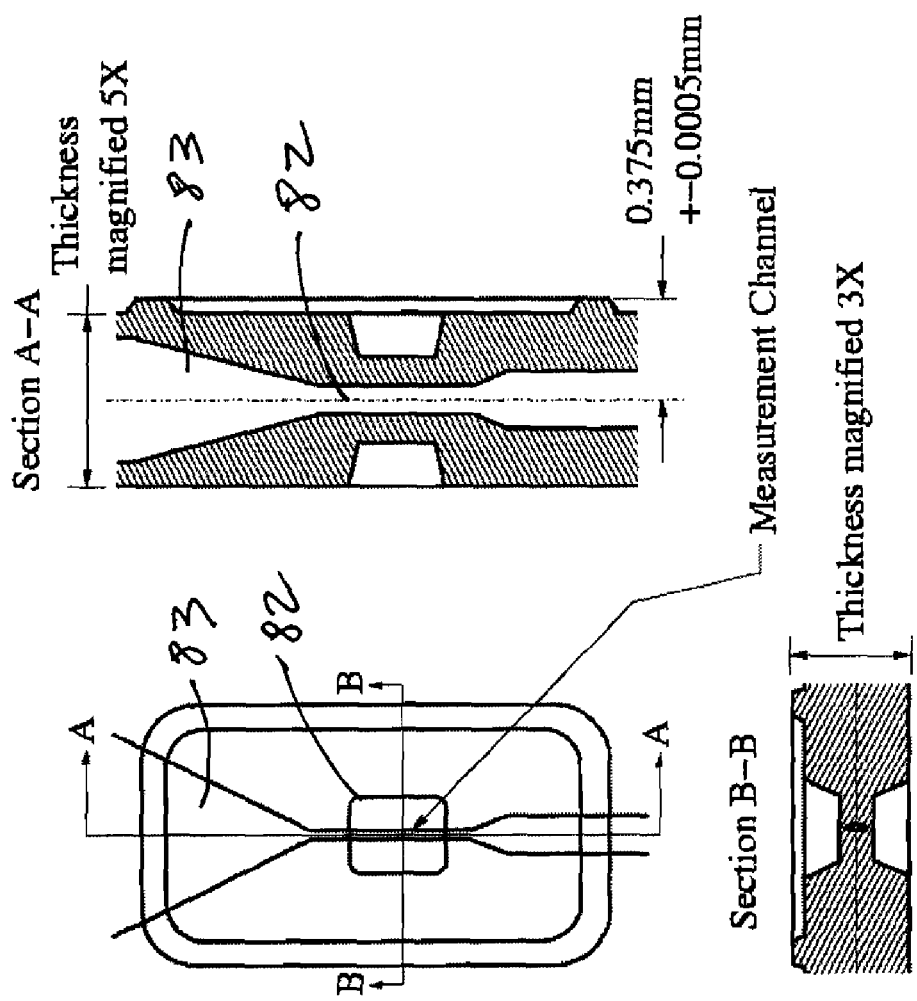
FIG. 10 shows an injection-molded measurement channel.

FIG. 10 shows an injection-molded measurement channel 82 with tight-tolerance between channel centerline and surface of the plastic part. The optic system may reference to the part surface to set a focal plane. To allow a fixed-position optic sensing system, the measurement channel 82 component may require tight tolerances. The maximum cross-section of the channel itself may be 0.200 (+0.020, −0.020) by 0.100 (+0.015, −0.015) mm. If the surface of a plastic part is used to register the optics system with respect to the centerline of the measurement channel 82, the z-axis dimension of the surface with respect to centerline of measurement channel (±0.005 mm) may be the tightest tolerance of the entire card. There may be a movable self-adjusting optic sensing system on the reader so that this tight tolerance is unnecessary if it is a significant cost factor.

Figure 11A:
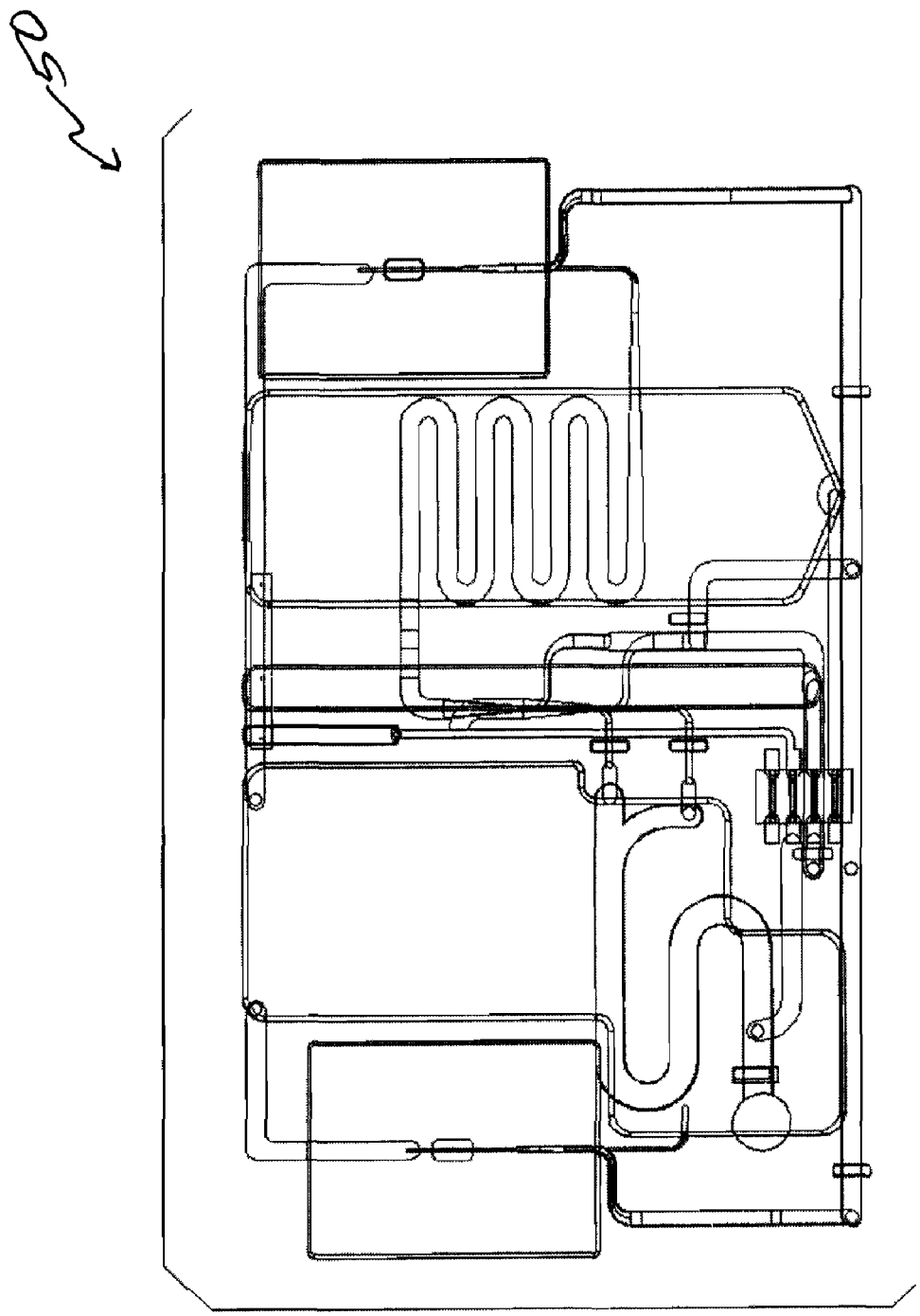
FIGS. 11a and 11b show a layout of components on an analyzer card.
Figure 11B:
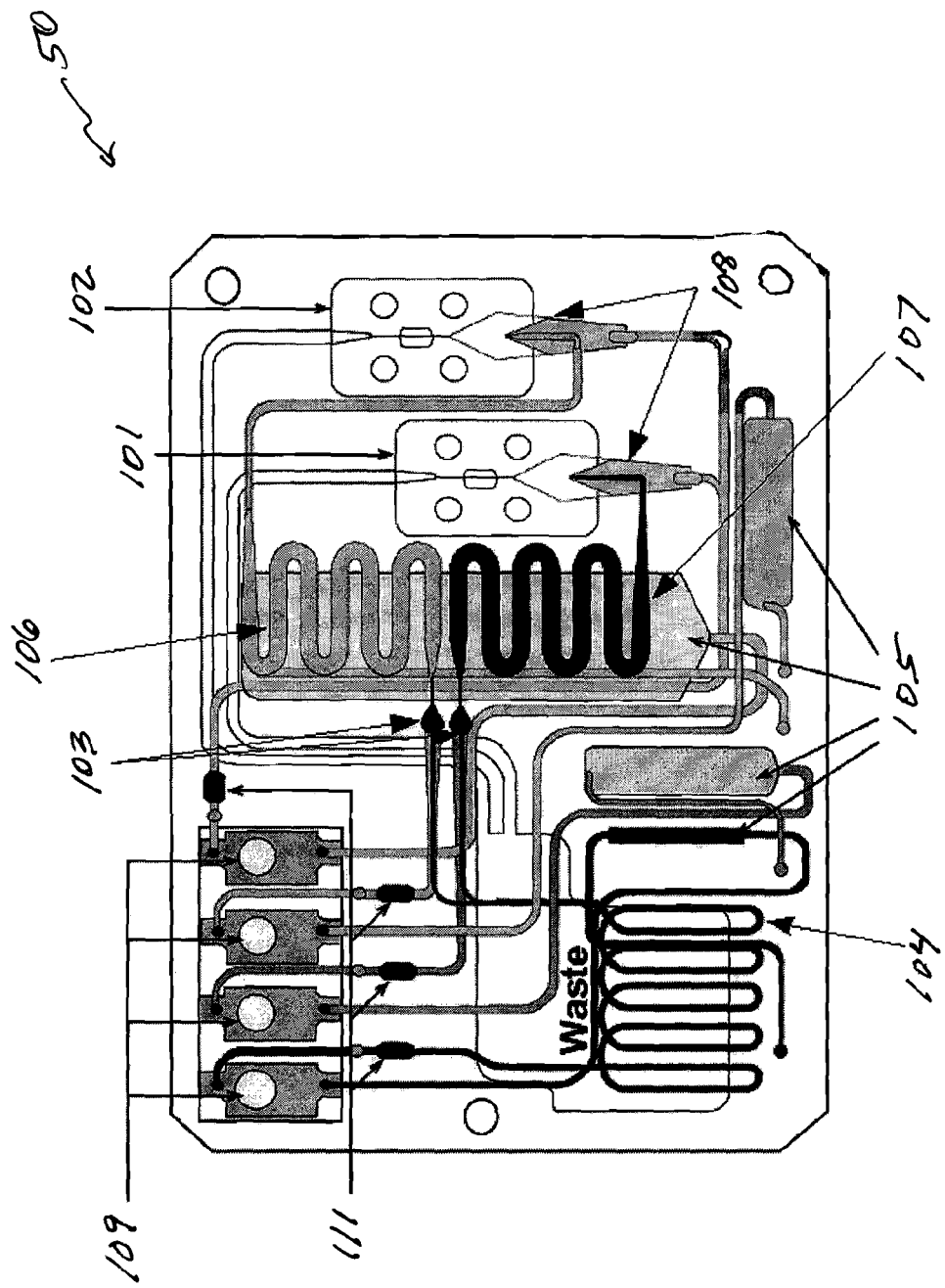

FIG. 11a shows an overlay view of network of channels, tanks, and flow sensors that may be noted in FIG. 5. The Figure shows the view of the channel network of the analyzer 50 as if the plastic parts were completely transparent. Many of the components may be correlated with those in FIG. 5. FIG. 11b shows another layout of card 50. It shows measurement channels 101 and 102, respectively, sample injectors 103, whole blood sample channel 104, reagent storage reservoirs 105, RBC dilution channel 106, WBC dilution channel 107, diluted sample injectors 108, flow sensors 109 and valves 111.

Figure 12:
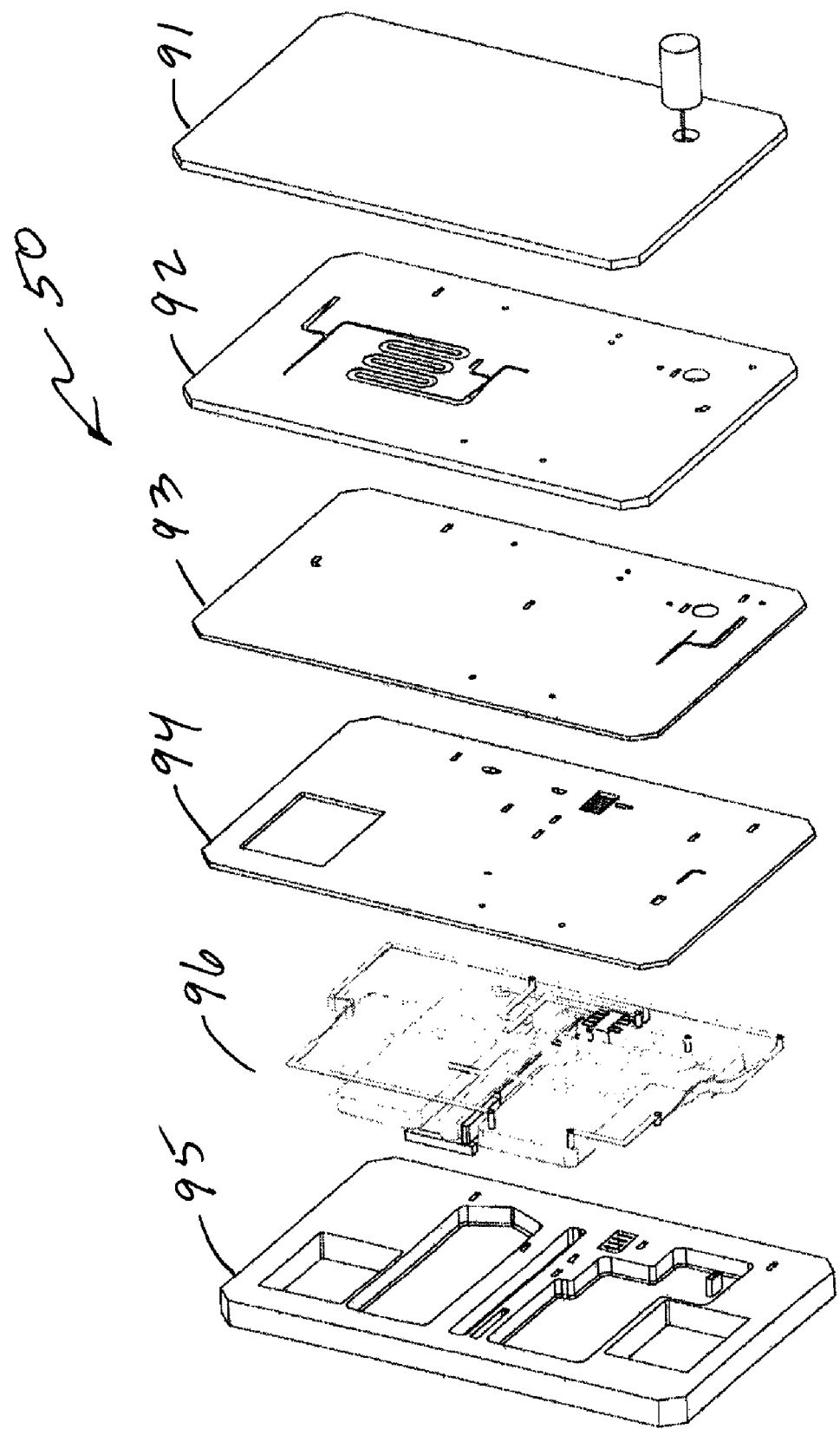
FIGS. 12 and 13 show a view of injection-molded parts that make up the analyzer card.
Figure 13:
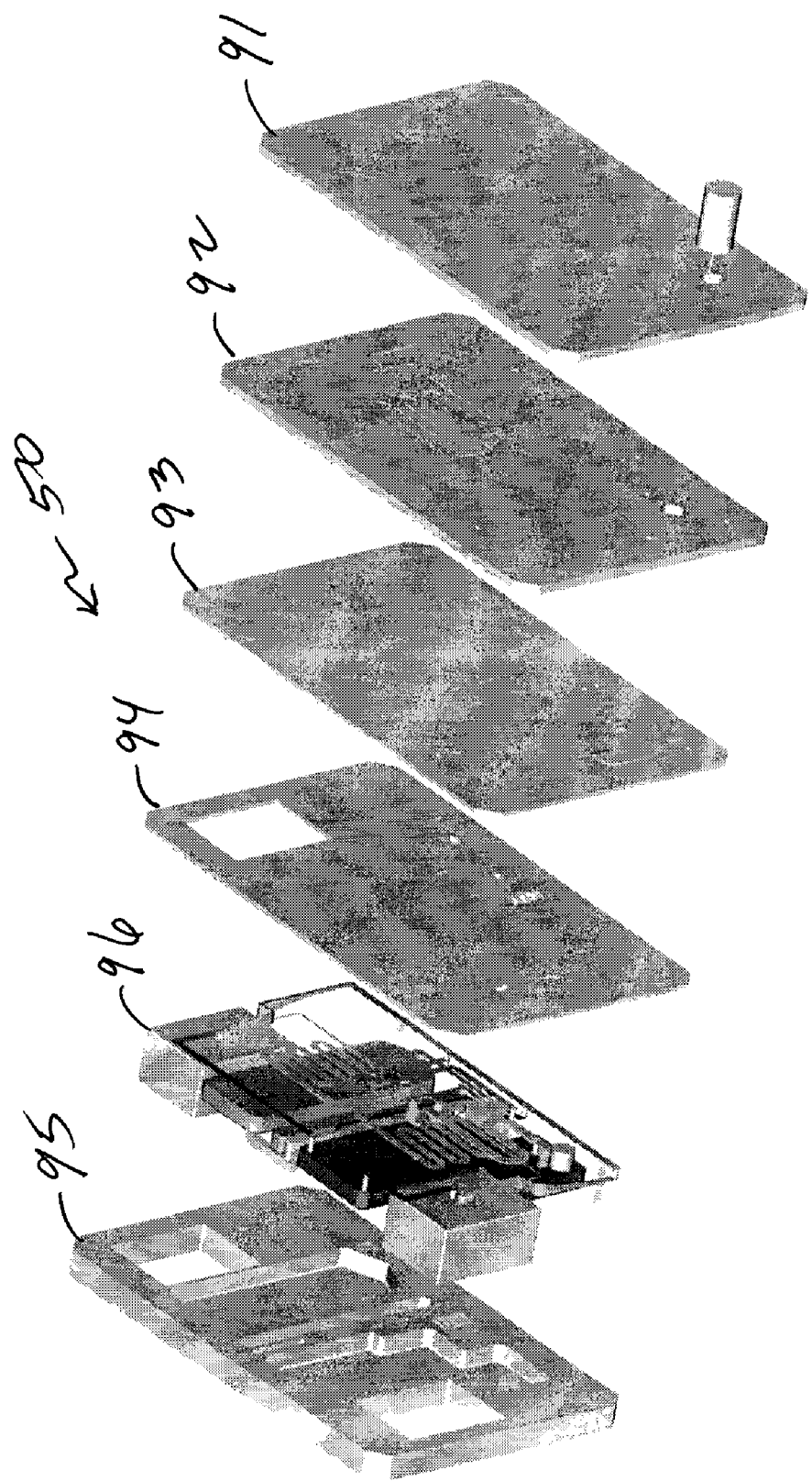

FIGS. 12 (a line drawing) and 13 (a solid view) show how the channel network is implemented as a series of injection molded plastic parts 91, 92, 93, 94 and 95 that make up the CBC card 50. Item 96 from the left is the channel network that may be realized in the parts. Portions of component 96 may be a result of the coming together of the plastic parts 91, 92, 93, 94 and 95. There may be bubble packs with there own wall for tanks of the system 50.

Reagent storage is an aspect of the system which may be considered. Six-month storage of liquid reagents may be achieved by placing fluid-filled blister packs in the tanks on the card during assembly. They may be opened during the assay by needle puncture as described herein. The volume of sheath fluid (sphering solution) tank for both WBC and RBC circuits may be about 2,000 µl. The volume of lysis solution tank may be about 240 µl. The volume of waste tank may be about 3,000 µl.

For fluid motion control, there may be a flow sensor sub-package that is comprised of four flow sensors, each with a fluid flow channel that has vias at both ends. The interface to this sub-package may be included on the card 50 as shown in FIG. 5. The sub-package vias may have elastomeric rings for leak-free fluid connections to the fluid network on the card 50. Seven valves for directing the fluids, including valving to switch sample flow between WBC and RBC circuits, may also be included on the card 50. The valves may have simple features.

The low-cost wet-interface card 50 may differ from the high-cost dry-interface card 50 in several ways. The wet-interface card may have no fluid storage tanks, only the waste tank remains to collect fluids injected into the card by a reader instrument during an assay. The wet-interface card may have no blister packs of reagents placed into the tanks during assembly, no flow sensors and no needle inserts in the sample injectors, except in the focusing chambers (i.e., two needle inserts instead of four).

As to materials, acrylic (polymethylmethacrylate, PMMA) is appealing as a molding material because of its known properties of optical transparency, relatively high surface energy (hydrophilicity), and chemical compatibility with the assay. A material with similar, or superior, properties may be substituted. No mold release components that lower surface energy (e.g., silicone oil) should be used. Two elastomer strips may be molded in to provide self-sealing interfaces for fluid injection through sharp needles (FIGS. 5, 7a and 7b).

As to bonding, the plastic parts may be bonded together so that leakage from the fluid channels is avoided. The bonding may include ultrasonic welding, an adhesive layer, a volatile solvent, or any other approach or material that can be implemented without changing the fluid channel geometry or introducing non-uniformity of the surface energy of the channel walls.

The card 50 was show as having five plastic parts. It could also be implemented in as few as two plastic parts that have larger lateral dimensions. The present card may contain 2-4 needle inserts. These may be eliminated by adding two additional layers to form the projecting tube shape in plastic instead of stainless steel.

A purpose of the sample/diluent injector structure of the cytometry card may be to create a thin ribbon of whole blood sheathed by a sphering solution. The thin ribbon shape may be desired because it allows the diluent solute (i.e., lysing or sphering agent) to rapidly diffuse to all erythrocytes and initiate its chemical process. The injector design may utilize a hollow needle to inject the blood sample into the center of the surrounding diluent.

A sample/diluent injector may be required on the cytometry card in both the WBC and RBC fluidic circuits. Since in the WBC circuit the red cells are to be lysed and in the RBC circuit the red cells are to be sphered, the injector may be called a sample/lyse injector in the WBC circuit and a sample/sphering-solution injector in the RBC circuit. There generally is no geometric difference between the two injectors and both may use the same whole blood sample flow rate. One difference may be that the flow rate of the sphering solution in the RBC card is 7.5 times the flow rate of the lysis solution in the WBC card.

The sample/diluent injector may use a physical structure to inject a sample stream into the center of a stream of diluent. A number of injector designs are possible, including curved injector needle into a straight pipe carrying diluent or a straight injector needle into a curved pipe. Here, one may chose the straight injector as a #31 gauge needle protruding into a curved channel. Considerations may include the following items. The injector should deliver sample to the center of the pipe cross-section. The injector tip should be located upstream of pipe cross-section changes designed to hydrodynamically focus the flow to match the next downstream channel. Less than half of the injector needle should protrude into the pipe so that it is easier to place and retain between the molded parts during assembly of the card. The fluid velocity of the sample leaving the injector should be less than the velocity of the surrounding diluent to prevent defocusing of the sample stream.

Initial conditions may include the following items. At the beginning, all of the channels should be filled with pure diluent. There should be no cells present and the fluid flow velocity should be zero.

Boundary conditions may include the following items. In the WBC situation, the flow rate of the diluent may be set at 60 μl/min. For the RBC situation, the diluent flow rate (sphering solution) may be set at 450 μl/min. In both situations, the sample flow rate should be 1.5 μl/min. These may be steady-state scenarios.

Additional parameters may include the following items. The density of the diluent may be 0.001 gm/μl, and the dynamic viscosity may be 0.001 Pa sec. The diffusion coefficient of the cells in the diluent may be assumed as $1\times10^{-6}$ mm$^2$/sec.

A simulation of the flow within the sample/diluent injector may be developed. The computational approach may include modeling of fluid motion by conservation of mass and momentum and modeling of molecular and advective diffusion by conservation of chemical species. A computational mesh of finite volumes may be employed to model the essential features of the card geometry.

Whole blood is 11 percent denser and 5.5 times more viscous than the aqueous diluent, but the blood sample may be diluted very soon after injection, rapidly becoming isolated cells in suspension. This may permit a simplification that ignores the initial higher density and viscosity of the sample blood and instead models the stream of blood as isolated cells suspended in diluent. This simplification may be implemented by treating the cells as if they were large molecules. Their motion may be modeled as a diffusion process and species conservation may be realized by application of the advection-diffusion equation. This equation may describe the rate of accumulation and depletion of a diffusing specie at each of the points within the fluid domain. It may be written as $$\frac{\partial c}{\partial t} = D\nabla^2 c - u\nabla c$$

where u is the local velocity vector, t is time, c is the normalized concentration of cells and D is their effective diffusion coefficient. The first term on the right hand side (rhs) may model molecular diffusion (i.e., Brownian motion) of the solute (cells) through the solvent (lysing or sphering solution). The second term on the rhs may model advective diffusion in which the solute is carried along in the flow of the solvent.

Calculation of the motion of the fluids as they merge in the sample/diluent injector may be accomplished by application of momentum conservation. The Navier-Stokes equation may be employed for an incompressible Newtonian fluid, which is a consequence of the application of Newton's second law to the fluid in the system. It may be written as $$\frac{\partial \rho u}{\partial t} + u \cdot \nabla \rho u + \nabla P - \mu \nabla^2 u = 0$$

which is a general equation that may be used for complex three-dimensional flow fields with vector velocity $u=(u_1, u_2, u_3)$, the pressure gradient $\Delta P$, the fluid density $\rho$, and the fluid viscosity $\mu$.

An analysis may indicate that the diluent flow becomes stabilized around the needle before it reaches its tip. Thus, the injector needle may protrude far enough into the surrounding channel. However, this protrusion length could be decreased by as much as half if there are reasons for seeking a shorter needle length.

The sample/diluent injector forms a cells stream that is a thin ribbon. Since red blood cells are typically 5.5 μm in diameter, even in the WBC card, the diffusing sphering or lysing agent would only need to penetrate 10 μm, or less than two cell diameters to reach the center of the cells stream. Thus, the sphering and lysing processes should not be diffusion limited. This same type of analysis may be performed for the focusing chamber downstream to characterize the focused cell stream as it proceeds into the optical measurement channel for counting.

In addition to the RBC and WBC cards, a card 33 for measurement and analysis of hemoglobin (HGB) may be provided for the hematology analyzer 10 (FIGS. 1 and 4). All three cards (FIGS. 2-4) could be incorporated in one card. The card may employ a wet interface with sample pusher fluid supplied by volumetric-based delivery from off-card reagent storage and flow sensors. The only on-card storage may be the waste tank 31 and the whole blood sample loop. Card 33 may also be regarded as a card 118 described herein.

An approach for measuring hemoglobin in whole blood may require preloading a well on card with lysis agents dissolved in methanol. This methanol solution may dry out and leaves behind a hydrophilic coating of lysis agents inside the well, ready to lyse the red cells when the whole blood sample is injected.

Figure 14:
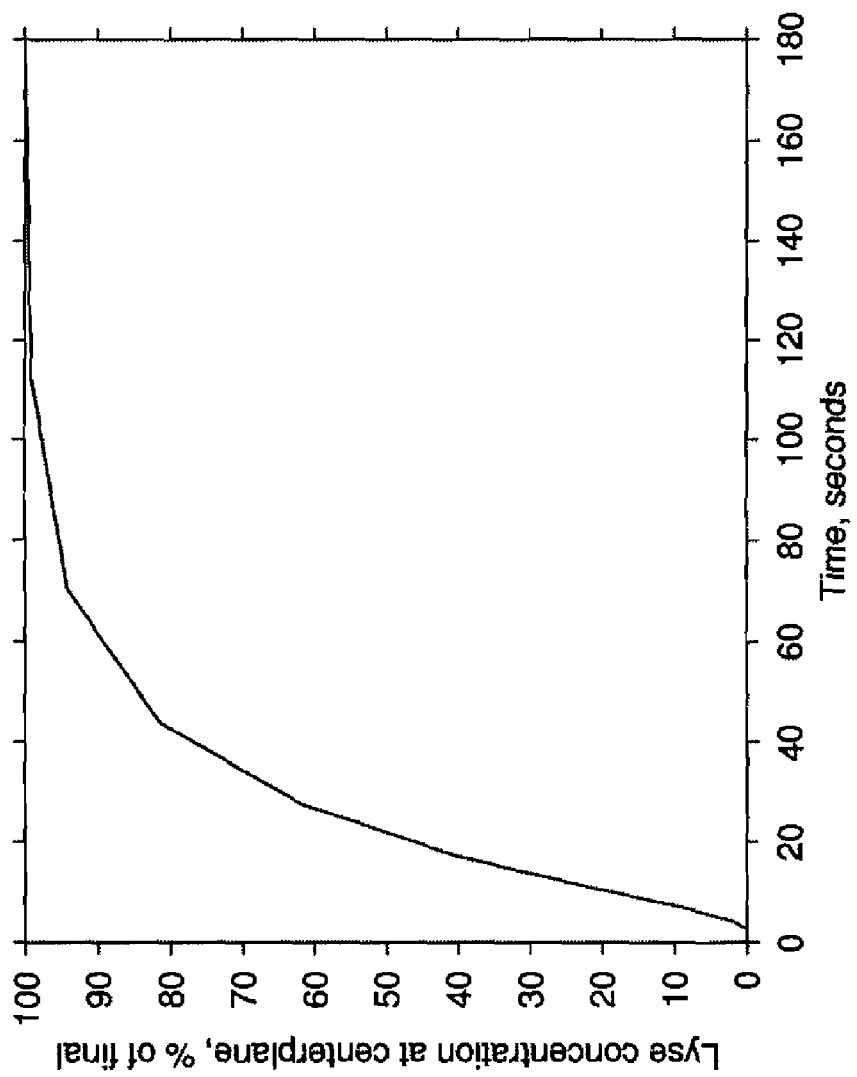
FIG. 14 is a plot of lyse concentration at a centerplane versus time.

In a graph of FIG. 14, it may be noted that the highest molecular weight lysis agent may be roughly the same size as Fluorescein and diffuse at approximately the same speed. The graph plots lyse concentration at a centerplane, in percent of final, versus time in seconds. Since blood viscosity is approximately 5.5 times that of water and diffusion speed is proportional to viscosity (according to the Stokes-Einstein relation), it may require over 1 minute for its concentration at the centerplane of a cuvette 115 (FIG. 15) to approach 90 percent of its equilibrium value.

Figure 15:
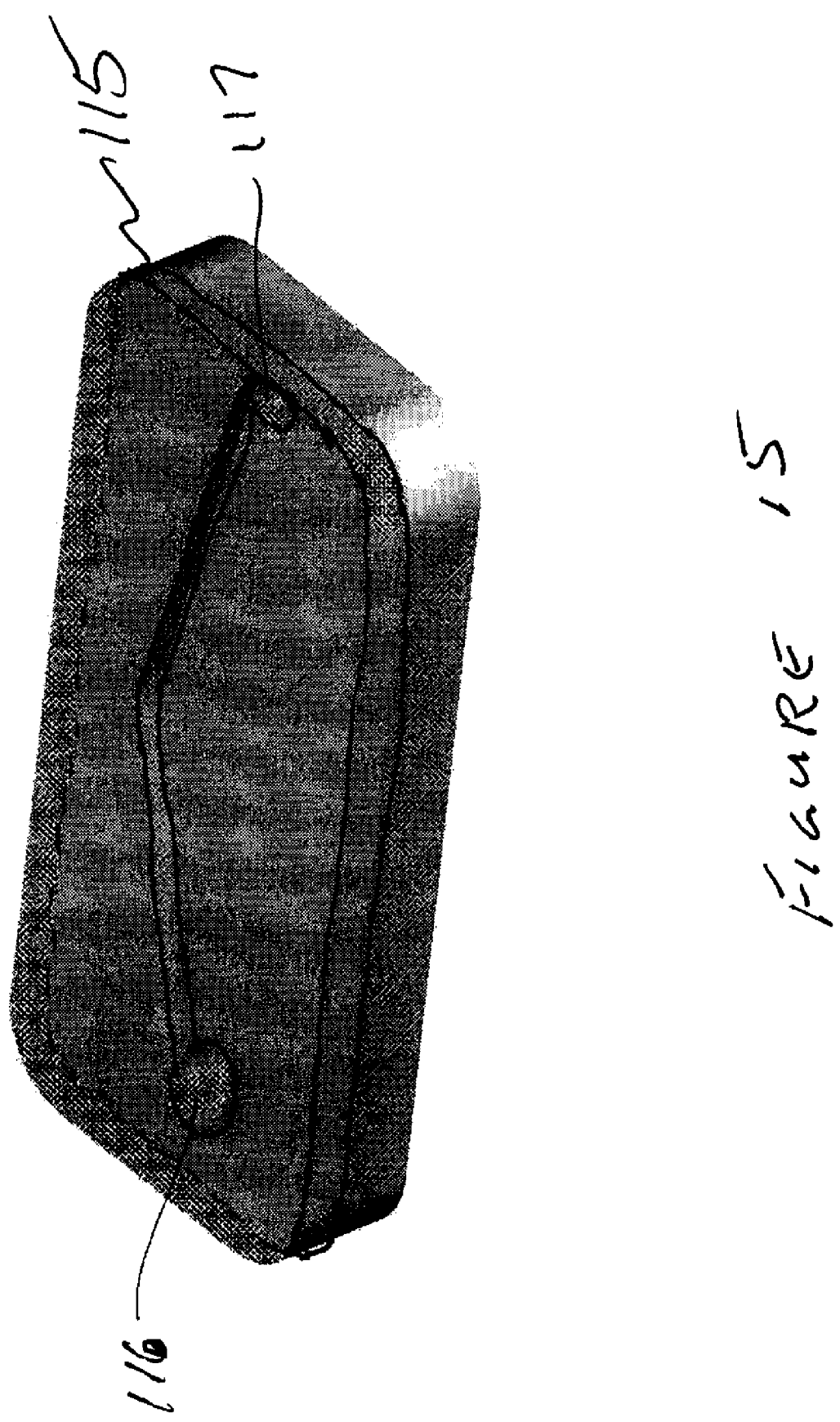
FIG. 15 shows a three-dimensional view of a cuvette for hemoglobin measurements.

A laminate or other kind of adhesive may be acrylic-based and probably not compatible with a solution that is more than 30 percent methanol. Once a methanol solution has dried, it does not necessarily pose a danger to card materials. So an approach may be to embed on the laminate or other kind of card prior to testing a polycarbonate or polystyrene cuvette 115 that has been precoated with the lysis agents. A window clearance (the inner dimension in the z-direction) of the cuvette 115 may be the critical path length for the absorbence measurement. The path length may be a significant source of error in the measurement. Since the total error should be limited to one percent, the path length may require a tolerance of less than one percent in the final integrated card design. For a round of testing, the path length in each cuvette 115 may be accurately measured to minimize it as a source of error. The path length may be within a range of between 150 and 300 microns, but in another design, a longer path length may allow a larger dimensional tolerance. The cuvette 115 may have a very simple shape, as shown in FIG. 15, which may be machined (or possibly molded) from polycarbonate stock as long as the path dimension is accurately measured for each device. The top of a well may be closed off by a flat sheet of polycarbonate that is solvent bonded or glued to the cuvette base.

Fluid communication between the laminate or other kind of card and the cuvette may be by the by two holes in its base, which is pressed against the exposed pressure sensitive adhesive layer of a second layer to form the fluidic seal. This may be similar to a flow sensor mounting approach, but the cuvette is less likely to leak since there is virtually no backpressure between the cuvette and the vented waste tank.

FIG. 15 shows a 3-dimensional view of the cuvette 115 with its cover plate shown as semi-transparent. The vias 116 and 117 on left and right, respectively, may provide fluidic connections to the card (FIG. 17) below the cuvette.

Figure 16:
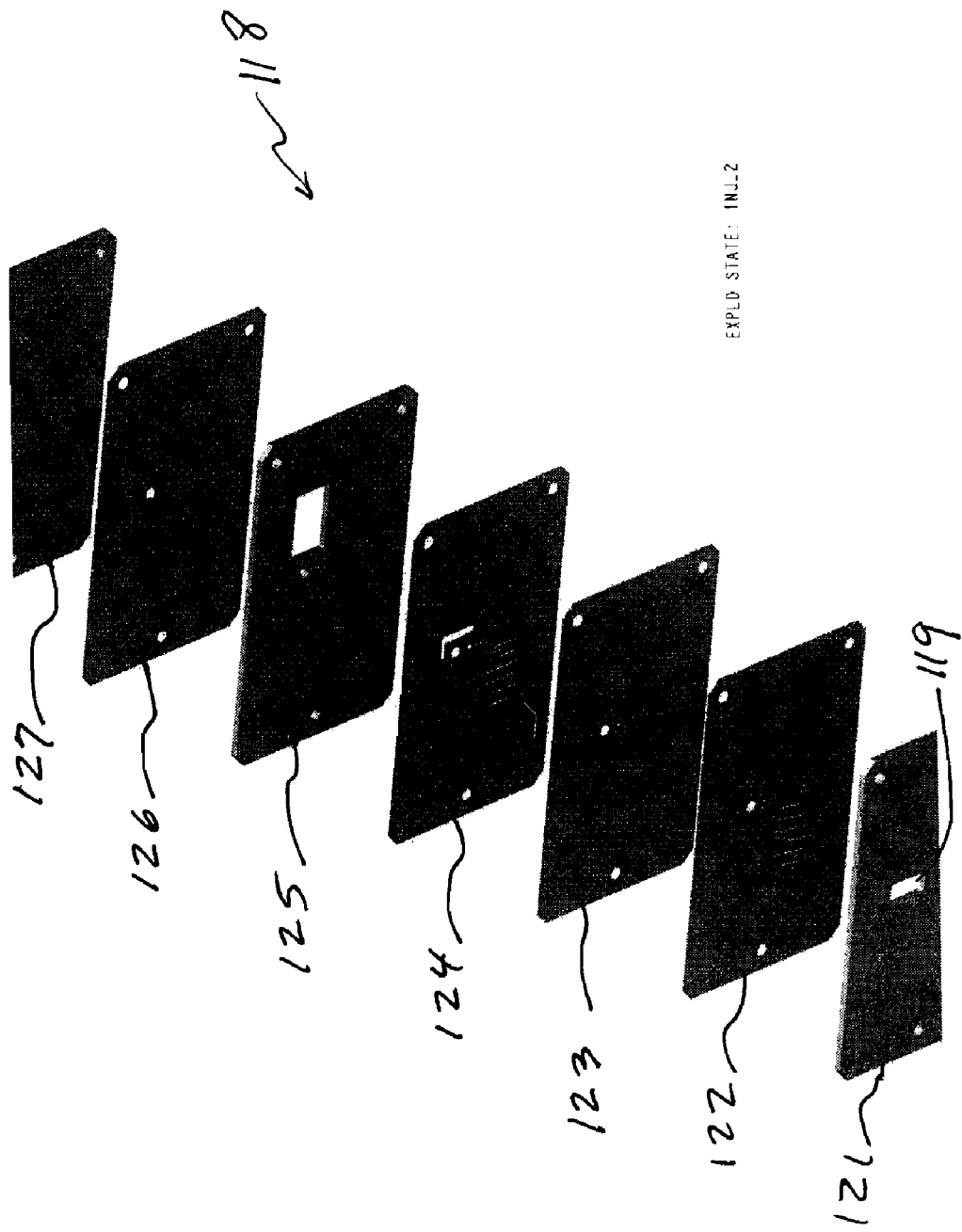
FIG. 16 shows a view of layers that compose a hemoglobin parameter measurement card.
Figure 17:
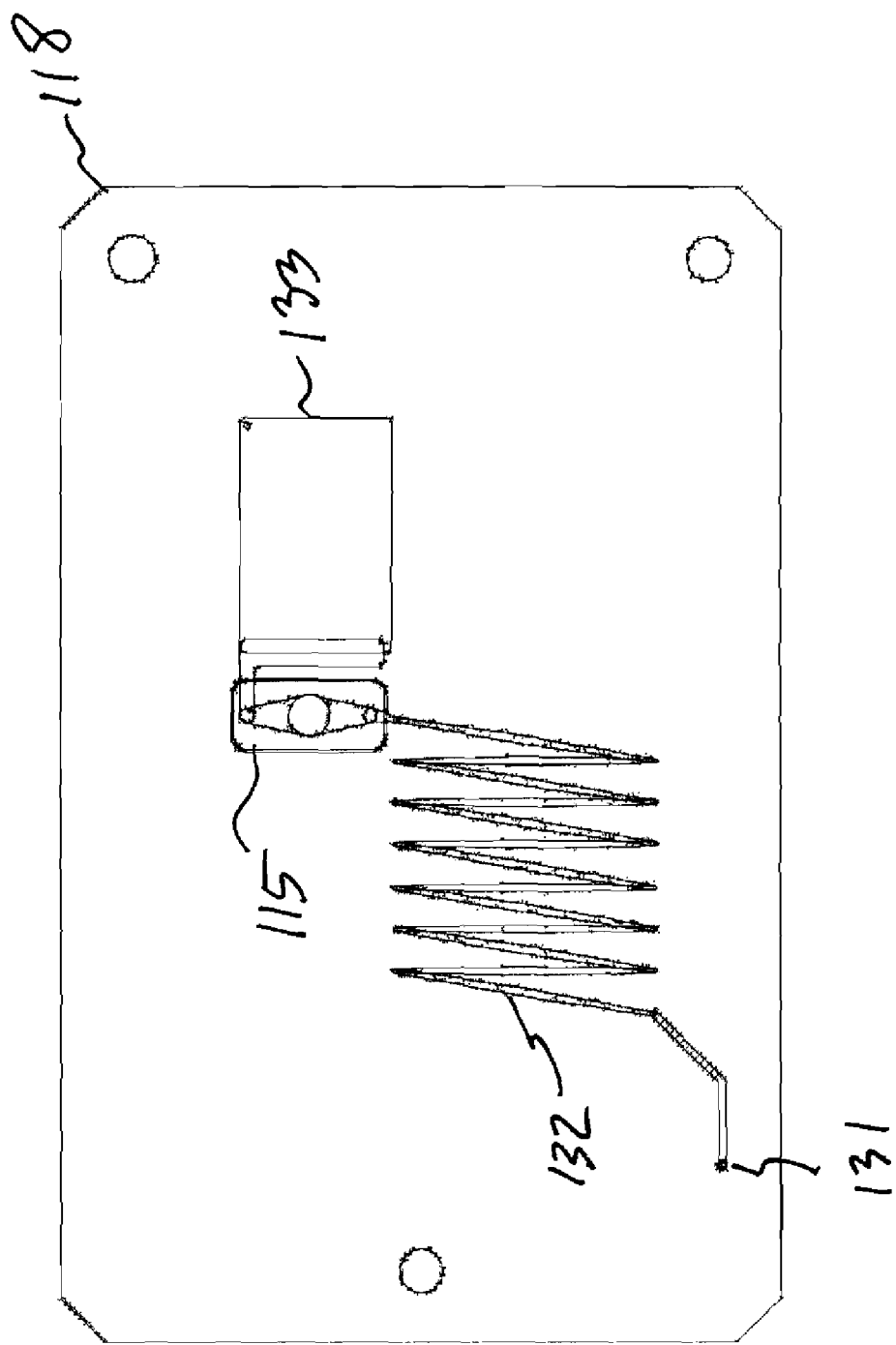
FIG. 17 shows a plan view of the hemoglobin parameter measurement card.

FIG. 16 shows an exploded view of the laminate, molded, or other kind of layers 121, 122, 123, 124, 125, 126 and 127 of the hemoglobin parameter measurement card 118. FIG. 17 shows the plan view of the hemoglobin card 118. The cuvette 115 may fit into a slot 119 in layer 121, which appears at the bottom of the stack as shown in FIG. 16, and may be bonded to the pressure-sensitive adhesive in the next higher layer, layer 122.

Before the light absorbence measurement of hemoglobin concentration approach is performed, the sample blood may be exposed to a reagent that lyses the red blood cells and alters the hemoglobin molecules to a uniform state. This reagent may be implemented as a dry powder on the surface of the cuvette 115. As the sample blood first flows over the cuvette surface, it may quickly absorb the lysis reagent powder. The absorbence measurement may be performed after the blood cells are lysed and the hemoglobin has reached a stable state.

In an alternative configuration, a lysing chamber, in which the reagent powder may be deposited, may be provided upstream of the cuvette 115. Since the cuvette may be free of reagent powder, a calibration absorbence measurement may be performed before the lysed blood enters the cuvette 115. This calibration may accommodate the card-to-card variation in light absorbence of the cuvette, itself.

Many of the components of the hemoglobin microfluidic circuit may include long and narrow channels with widths, volumes, and layer thicknesses as specified herein. The height dimensions may be small and have the tightest tolerances since they affect pressure loss, sedimentation rate, and diffusion speed in the channels. The channel widths and lengths are nominal, but volume tolerances may be specified.

A sample may be whole blood loaded into the sample loop 132 through an inlet port 131. The port 131 may be sized to match the syringe needle used for loading the blood. An alternative interface may have needles on the manifold that penetrate elastomeric septums on the card 118. The base of these needles may press against the elastomer, providing a low-compliance seal during operation. After the assay, the septum may self-seal and prevent leakage while handling the card 118 for disposal.

The sample loop 132 may be sized long and thin for several reasons. The first may be to match the sample loop on the RBC card and ease integration of the HBG channel into the three-channel CBC card. Another may be to ensure a more complete sweep of sample blood by the pusher fluid. If the sample loop 132 were a short wide channel, the pusher fluid would possibly sweep through the channel center leaving behind much of the sample blood along the walls.

The cuvette 115 thickness may be an optical path. This may be a critical dimension on the card. Its volume may be chosen for easier integration into the three-channel CBC card. There may 10 microliters of sample in the card specification which may be shared with the RBC and WBC channels in the three-channel CBC card. The round body center may be chosen to interface with the optics and this is a region where fluid thickness may be critical. The angle shapes that connect the body center to the inlet 116 and outlet 117 vias may be chosen to avoid sudden changes in channel cross-section that tend to trap bubbles during wetout. The cuvette 115 may be oriented with the exit upwards so that gravity effects will help purge bubbles during wetout.

The cuvette 115 is an insert which may be placed on card 118 prior to test. Red cells may be lysed in the cuvette 115. After the hemoglobin measurement is complete, the sample may be pushed into a waste tank 133. With a little more detail, an analysis process may begin with preloading whole blood. Two microliters of sample may be pushed with pusher fluid at 12 microliters/minute into cuvette for $0<t<10$ sec. A pause may be in order for 60-120 seconds while lysis occurs. Then an absorbence measurement may be performed. The sample may then be pushed to the waste tank 133.

The portions of the card 118 that store fluids that may have specific tolerances may include the whole blood storage loop 132 which has a tolerance range between 15 and 18 microliters and a nominal volume of 16 microliters. The waste tank 133 may have a tolerance range between 26 and 32 microliters and a nominal value of 28 microliters. The cuvette may have a tolerance range between 1.9 and 2.1 microliters and a nominal value of 2 microliters. The cuvette 115 is a separately fabricated insert and its volume is not part of the laminate or other kind of card 118.

There are generally no critical channel width tolerances other than those needed to ensure channels and vias connect properly. There may be channel features that have a relatively large compliance and introduce system dynamics. These areas may include the sample loop 132 and the waste tank 133. Much of this compliance may be rectified by use of thicker material for layers 121 and 127. The table in FIG. 18 shows a list of materials and thickness tolerances that may be used for layers 121 through 127.

Surface energy should be uniform throughout the channels to be wetted. An overall value of between 40 and 60 dynes/cm may be appropriate for any card, but the uniformity of surface energy of a particular card should be limited to a few dynes/cm. This may be demonstrated by a bubble-free wetout of the channels in which the wetting velocity is nearly constant over each constant channel cross-section. Channel wetting should not exhibit pauses followed by wetting velocity surges leaving air bubbles trapped behind the fluid front.

Quality control of card 118 may include the following metrics. The card may meet tolerances on key dimensions of card design, have uniform surface properties in channels, verified by bubble-free wetout of randomly selected sample cards in each manufacturing lot, be free of dust particles larger than 1 µm, hair, and the like, in the microchannels by microscopic inspection. The latter may avoid channel blockage and prevent the interference of foreign bodies during hemoglobin measurement. There should be sufficient adhesion of adhesive layers such that pressurization of card channels of 1 psi gage does not cause leakage of fluid between card layers.

Other items that may be considered relative to fabrication of an HGB card 118. There may be active gap finding where metallic coatings enable detection of separation distance by capacitance. There may be dry reagent loading where the reagent is printed on molded parts before assembly of the card. There may be active pumping where blood is loaded into cuvette by an active pump.

The core in a flow channel of an analyzer may be controlled in various ways. For instance, there may be active core positioning by microjets. The core may be positioned within the optical channel by lateral flow emitted from control jets on the channel sidewalls. Another approach may include a dual-pump sheath. Instead of geometrically locating the core, the core may be positioned by two parallel and opposing flows of sheath fluid that enter the optical channel laterally and surround and compress the sample stream. This approach may replace the focusing chamber and remove the problem of trapped air bubbles during wet-out.

Figure 19:
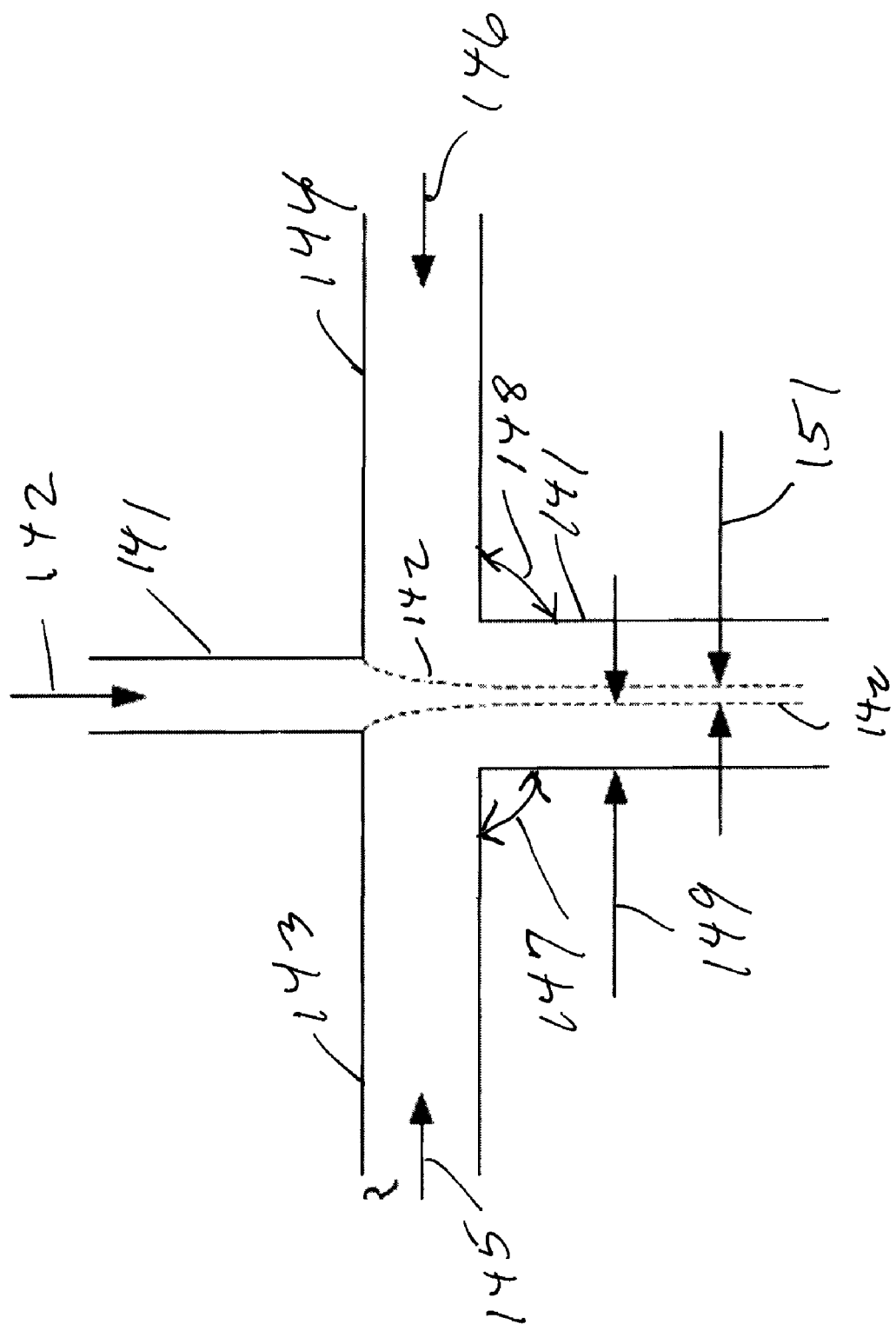

FIGS. 19-23 show illustrative examples of 3-D hydrodynamic focusing. FIG. 19 shows a flow channel 141 having a sample flow or core 142. There may be sample core 142 formatting with another fluid. The sample flow 142 may be controlled and/or focused with other fluid flows 145 and 146 entering the flow channel 141 through control channels 143 and 144, respectively. Channels 143 and 144 may be coupled to flow channel 141 on the sides. The channels 143 and 144 have angles 147 and 148, respectively, of about 90 degrees relative to the flow channel 141 longitudinal axis. However, angles 147 and 148 may be 45, 120 degrees, or other magnitudes. Angles 147 and 148 may have different or the same magnitudes. The fluid flows 145 and 146 may be a sheathing, sphering or lysing fluid. The fluid for flows 145 and 146 may be other kinds of fluids. The fluids for flows 145 and 146 may be different from each other. The fluids of flows 145 and 146 may be a mix of various fluids.

The sample core 142 position 149 may be adjusted by changing a ratio of the velocity of fluid flow 145 relative to the velocity of fluid flow 146. The sample core 142 width 151 may be adjusted by changing the ratio of the sample fluid 142 velocity relative to the velocity of the fluid flow 145 and/or fluid flow 146. There may be other fluid flow in addition to flows 145 and 146 for formation and/or control of core 142.

Figure 20:
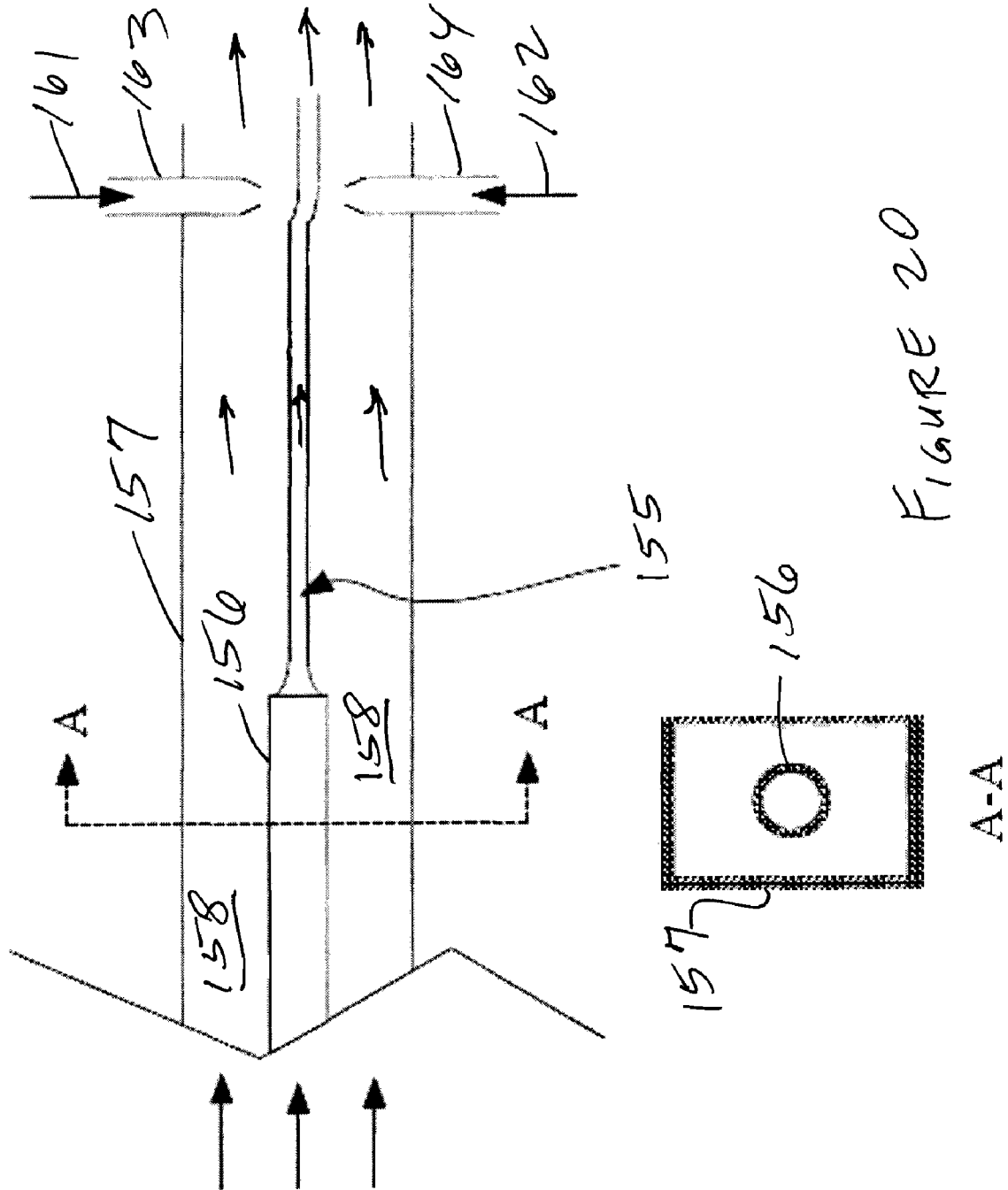

FIG. 20 shows formation and/or control of a sample core 155 from a tube, injector or channel 156. This injector 156 may be positioned within a flow channel or focusing chamber 157. Core 15 may surrounded by another fluid 158. Fluid 158 may be of a sheathing, sphering or lysing flow. Fluid 158 may be another fluid or a combination of fluids. Sample core 155 may be controlled relative to position and diameter by control steering fluids 161 and 162 flowing in through ports, jets or microjets 163 and 164, respectively. The microjets 163 and 164 may be situated at nearly any angle relative to the flow direction of the sample core 155. There may be one or more jets with control steering fluid flows. The steering fluid may be the same fluid or a different fluid relative to the fluid of flow 158.

Figure 21:
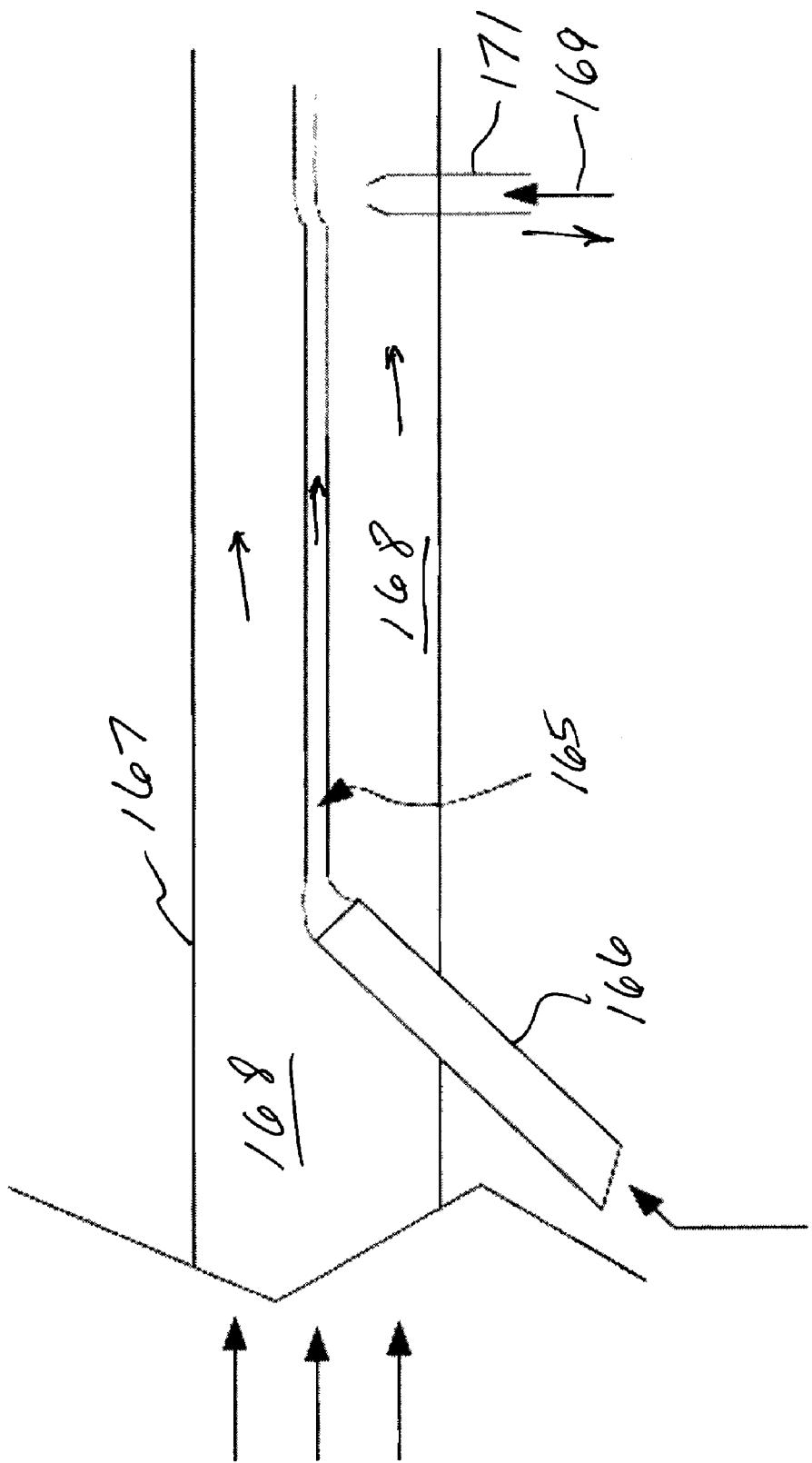

FIG. 21 shows a formation and/or control scheme of a sample core 155 flowing from a tube, channel or injector 166 that may be positioned at an angle relative to the longitude dimension of flow channel 167. The angle may be one of various magnitudes. Sample core 165 may have a flow of a fluid 168 around it in a sense of hydrodynamic focusing. However, the position of sample core 165 may be altered by a control steering fluid 169 from a jet 171. Core 165 may tend to move towards jet 171 because of gravity and weighty cells in the sample core. The fluid 169 may offset such effect. The jet 169 may pull fluid out from the channel 167, as well as provide fluid into the channel, for varied control of the core 165. There may be one or more jets with control steering fluid. Fluid 168 may be a sheathing, sphering or lysing fluid, or some other fluid or a combination of various fluids. The control steering fluid 169 may be the same as fluid 168, or different from fluid 168.

Figure 22:
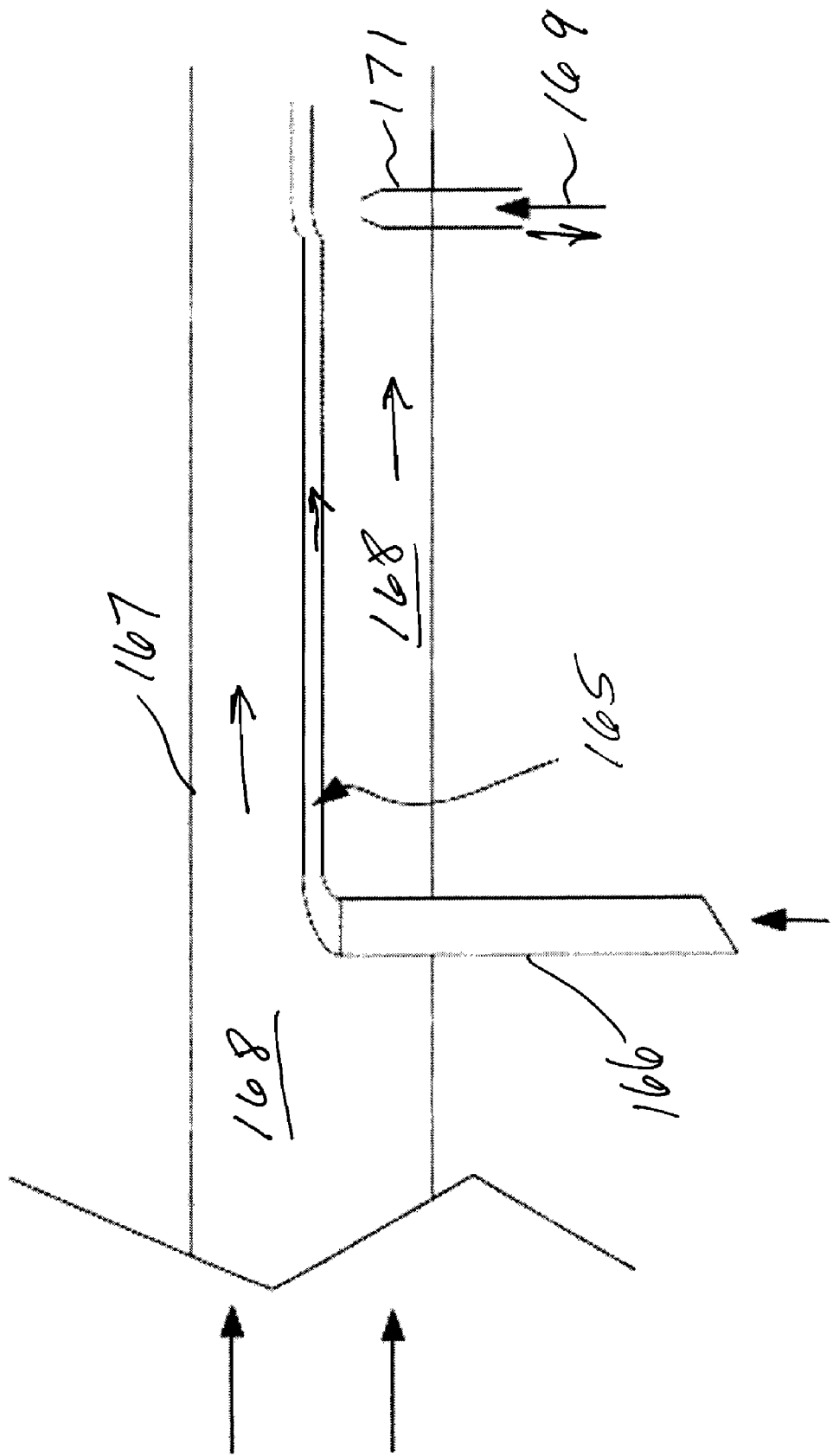

FIG. 22 shows a formation and/or control configuration for the sample core 165 similar to a configuration of FIG. 21, except that the tube, channel or injector 166 may be positioned perpendicular relative to the longitude axis of flow channel 167. One advantage over other positions is that this perpendicular position of injector 166 may let the cells be more rigorously ripped off from the end of the injector and prevent clumps of cells being in the sample core 165. The properties and characteristics of the configuration in FIG. 21 may be applicable to that of FIG. 22.

FIG. 23 shows a configuration that may appear similar to that of FIG. 22. Its injector 176 may have a first portion 177 that appears to be perpendicular to the direction of the flow of fluid 168 and the longitude axis of channel 167 like that of injector 166 in FIG. 22. However, injector 176 appears to have a second portion 178 that is approximately perpendicular to portion 177. Control or position of core flow 175 may be effected by movement of injector 176. The angles of portions 177 and 178 may be independently varies or adjusted relative to the direction of the flow of fluid 168.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A molded fluidic circuit card comprising:
a first channel having a longitudinal axis and a first fluid flow;
a second channel situated in the first channel, the second channel introducing a sample core flow within the first fluid flow;
a third channel coupled to the first channel and having a longitudinal axis at an angle relative to the longitudinal axis of the first channel;
a fourth channel coupled to the first channel and having a longitudinal axis at an angle relative to the longitudinal axis of the first channel, the fourth channel positioned at a location relative to the third channel to achieve three-dimensional focusing of the core sample;
a first fluid reservoir coupled to the third channel;
a second fluid reservoir coupled to the fourth channel;
a flow rate control box in communication with the third and fourth channels, the flow rate control box controlling the flow of a second fluid from the first fluid reservoir through the third channel and into and through the first channel and the flow rate control box controlling the flow of a second fluid from the second fluid reservoir through the fourth channel and into and through the first channel;
wherein the flow rate control box controls a velocity of fluid flow in the third channel relative to a velocity of fluid flow in the fourth channel to adjust the sample core flow in three dimensions, thereby achieving three-dimensional focusing of the sample core flow;
wherein the first, second, third, and fourth channels and first and second fluid reservoirs are molded components in the fluidic circuit card.

2. The card of claim 1, wherein the fluidic circuit card comprises a cytometer.

3. The card of claim 1, wherein a position of the sample core flow is adjustable by changing a ratio of a velocity of the fluid from the third channel and a velocity of the fluid from the fourth channel.

4. The card of claim 1, wherein a size of the sample core flow is adjustable by changing a ratio of a velocity of the sample core flow and a velocity of the fluid from the third channel and the fourth channel.

5. A molded microfluidic analyzer card comprising:
a flow channel;
a sample core flow situated in the flow channel;
a plurality of control channels each having a longitudinal axis coupled to the flow channel configured to introduce a steering fluid into the flow channel to adjust the sample core flow;
a flow rate control box configured to control fluid flow in the plurality of control channels;
wherein each of the plurality of control channels is positioned at an angle to the longitudinal axes of the remaining plurality of control channels;
wherein the flow rate control box adjusts a position of the sample core flow by changing a ratio of the velocities of the steering fluids entering the flow channel from a first and a second control channel relative to each other;
wherein the flow rate control box adjusts a size of the sample core flow by changing a ratio of the velocities of the steering fluids entering the flow channel from a first and a second control channel relative to each other;
wherein the flow channel and the plurality of control channels are molded components in the microfluidic card.

6. The card of claim 5, wherein the flow channel is a cytometer flow channel.

7. The card of claim 5, wherein:
the flow channel includes a flow of a first fluid; and
the sample core flow is a sample core in the flow of the first fluid.

8. The card of claim 7, wherein the first fluid is a reagent.

9. A molded fluidic circuit card comprising:
a first channel having a longitudinal axis;
a second channel disposed in the first channel;
a first control channel coupled to the first channel and having a longitudinal axis at an angle relative to the longitudinal axis of the first channel; and
a second control channel coupled to the first channel and having a longitudinal axis at an angle relative to the longitudinal axis of the first channel, the second control channel positioned at an angle relative to the longitudinal axis of the first control channel; and
a flow rate control box in communication with the first control channel and the second control channel; and
wherein:
the first channel includes a first fluid flow;
the second channel introduces a sample core flow within the first fluid flow;
the first control channel is coupled to a first fluid reservoir and the second control channel is coupled to a second fluid reservoir such that a second fluid may flow from the first and second fluid reservoirs through the first and second control channels into the first channel in a single direction to adjust the sample core flow; and
the flow rate control box controls a velocity of fluid flow in the first control channel relative to a velocity of fluid flow in the second control channel to adjust the sample core flow in three dimensions, thereby achieving three-dimensional focusing of the sample core flow;
wherein the first and second channels, first and second control channels, and first and second fluid reservoirs are molded components in the fluidic circuit card.

10. The card of claim 9, wherein a position of the sample core flow is adjustable by changing a ratio of a velocity of the fluid from the first control channel and a velocity of the fluid from the second control channel.

11. The card of claim 9, wherein a size of the sample core flow is adjustable by changing a ratio of a velocity of the sample core flow and a velocity of the fluid from the first control channel and the second control channel.

* * * * *